(12) United States Patent
Scott et al.

(10) Patent No.: US 8,800,366 B2
(45) Date of Patent: Aug. 12, 2014

(54) ROBOTIC EXOSKELETON FOR LIMB MOVEMENT

(71) Applicants: Stephen H. Scott, Kingston (CA); Ian E. Brown, Kingston (CA); Stephen J. Ball, Kingston (CA)

(72) Inventors: Stephen H. Scott, Kingston (CA); Ian E. Brown, Kingston (CA); Stephen J. Ball, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 13/675,609

(22) Filed: Nov. 13, 2012

(65) Prior Publication Data

US 2013/0158438 A1  Jun. 20, 2013

Related U.S. Application Data

(62) Division of application No. 12/149,462, filed on May 1, 2008, now Pat. No. 8,347,710.

(60) Provisional application No. 60/924,135, filed on May 1, 2007.

(51) Int. Cl.
| | |
|---|---|
| *A61B 5/103* | (2006.01) |
| *A61B 5/11* | (2006.01) |
| *A61F 5/00* | (2006.01) |
| *A63B 21/00* | (2006.01) |
| *A61B 5/00* | (2006.01) |
| *A61H 1/02* | (2006.01) |
| *B25J 9/00* | (2006.01) |

(52) U.S. Cl.
CPC ......... *A61B 5/103* (2013.01); *A61H 2201/1676* (2013.01); *A61H 2201/1635* (2013.01); *A61H 2201/1602* (2013.01); *A61B 5/4528* (2013.01); *A61H 2201/1633* (2013.01); *A61H 2201/164* (2013.01); *A61H 1/0237* (2013.01); *A61H 1/0274* (2013.01); *A61H 2201/1638* (2013.01); *A61H 2201/5084* (2013.01); *A61H 2201/1659* (2013.01); *A61H 2201/5064* (2013.01); *B25J 9/0006* (2013.01); *A61B 5/1038* (2013.01); *A61H 1/0262* (2013.01); *A61H 2201/1215* (2013.01)
USPC ................ 73/379.01; 414/2; 414/5; 600/587; 600/595; 601/33; 601/34; 602/16; 602/20; 602/23; 73/865.4

(58) Field of Classification Search
USPC ............... 414/2, 5; 600/587, 595; 601/33, 34; 602/16, 20, 23; 73/379.01–379.03, 73/865.5
See application file for complete search history.

(56) References Cited

U.S. PATENT DOCUMENTS

| | | |
|---|---|---|
| 4,566,440 A | 1/1986 | Berner et al. |
| 4,878,663 A | 11/1989 | Luquette |

(Continued)

FOREIGN PATENT DOCUMENTS

| | | |
|---|---|---|
| CN | 101125112 A | 2/2008 |
| CN | 201019972 Y | 2/2008 |
| EP | 0597623 A1 | 5/1994 |
| WO | WO2004058458 A1 | 7/2004 |
| WO | WO2006058442 A1 | 6/2006 |

OTHER PUBLICATIONS

Ball, S.J., et al., "A planar 3DOF robotic exoskeleton for . . . assessment", Proc. IEEE Int. Conf. on Eng. in Medicine and Biology Society, Lyon, France, 4024-4027 (Aug. 2007).

(Continued)

*Primary Examiner* — Sean Dougherty
(74) *Attorney, Agent, or Firm* — Stephen J. Scribner

(57) ABSTRACT

This invention relates to a robotic exoskeleton comprising mechanical linkages that couple to one or more selected joints of a limb of a subject. The robotic exoskeleton may be provided with means for obtaining data respecting angular position, torque, and/or acceleration of at least one of the joints or the links of the mechanical linkages, and may be used for assessing, studying, diagnosing a deficit, and/or treating an impairment in sensorimotor function of a limb of a subject.

18 Claims, 22 Drawing Sheets

(56) References Cited

U.S. PATENT DOCUMENTS

| | | | |
|---|---|---|---|
| 5,163,451 | A | 11/1992 | Grellas |
| 5,231,998 | A | 8/1993 | Rosen et al. |
| 5,280,783 | A | 1/1994 | Focht et al. |
| 5,333,604 | A | 8/1994 | Green et al. |
| 5,466,213 | A | 11/1995 | Hogan et al. |
| 5,476,441 | A | 12/1995 | Durfee et al. |
| 5,865,714 | A | 2/1999 | Marlowe |
| 5,899,869 | A | 5/1999 | Barrack et al. |
| 6,155,993 | A | 12/2000 | Scott |
| 6,741,911 | B2 * | 5/2004 | Simmons ............... 700/245 |
| 6,796,926 | B2 | 9/2004 | Reinkensmeyer et al. |
| 6,805,606 | B1 | 10/2004 | Kellum |
| 6,821,233 | B1 | 11/2004 | Colombo et al. |
| 8,070,659 | B2 | 12/2011 | Gagnon et al. |
| 2003/0115954 | A1 | 6/2003 | Zemlyakov |
| 2003/0120183 | A1 * | 6/2003 | Simmons ............... 600/595 |
| 2004/0254679 | A1 * | 12/2004 | Nagasaka ............... 700/245 |
| 2008/0009771 | A1 | 1/2008 | Perry |
| 2008/0255488 | A1 | 10/2008 | Agrawal et al. |

OTHER PUBLICATIONS

Ball, S.J., et al., "Designing a robotic exoskeleton for . . . rehabilitation", 30th Cdn. Medical and Biological Eng. Conf., Toronto, Canada (Jun. 2007).

Ball, S.J., et al., "MEDARM: a rehabilitation robot with 5DOF at . . . complex", Proc. IEEE/ASME Int. Conf. on Advanced Intelligent Mechatronics, Zurich, Switzerland (Sep. 2007).

Carignan, C., et al., "Design of an arm exoskeleton with scapula motion for . . . rehabilitation", Proc. 12th Int. Conf. on Advanced Robotics, Seattle, USA, 524-531 (Jul. 2005).

Centre for Rehabilitation and Engineering Studies (CREST), University of Newcastle upon Tyne, Motorized Upper Limb Orthotic Systems (MULOS), Apr. (1998) (Document downloaded from website.).

International Search Report and Written Opinion of International Searching Authority for corresponding International Application No. PCT/CA2008/000839.

Mihelj, M., et al., "ARMin—toward a six DoF . . . robot", Proc. IEEE/RAS-EMBS Int. Conf. on Biomedical Robots and Biomechatronics, Pisa, Italy, 1154-1159 (Feb. 2006).

Mihelj, M., et al., "ARMin II—7 DoF rehabilitation robot: mechanics and kinematics", Proc. IEEE Int. Conf. on Robotics and Automation, Rome, Italy, 4120-4125 (Apr. 2007).

Nef, T., et al., "ARMin—design of a novel arm rehabilitation robot", Prod. IEEE Int. Conf. on Rehabilitation Robotics, Chicago, USA, 57-60 (Jun. 2005).

Perry, J.C., et al., "Design of a 7 degree-of-freedom . . . exoskeleton", Proc. IEEE/RAS-EMBS Int. Conf. on Biomedical Robots and Biomechatronics, Pisa, Italy (Feb. 2006).

Supplementary European Search Report for European Application No. EP08748241.0 filed May 1, 2008.

* cited by examiner

ROBOTIC EXOSKELETON FOR LIMB MOVEMENT

RELATED APPLICATIONS

This is a divisional application of U.S. patent application Ser. No. 12/149,462, filed on May 1, 2008, now U.S. Pat. No. 8,347,710, issued on Jan. 8, 2013, and claims the benefit of the filing date of U.S. Provisional Patent Application No. 60/924,135, filed on May 1, 2007, the contents of which are hereby incorporated by reference in their entirety.

FIELD OF THE INVENTION

This invention relates generally to a robotic exoskeleton that attaches to a subject's limb, for use in areas such as assessment, rehabilitation, and/or research involving motor function. In particular, the invention relates to a robotic exoskeleton that provides off-axis mechanical coupling of one or more joints of a limb of a subject. The invention also relates to a robotic exoskeleton having coupling between two or more joints, wherein spacing between joints is easily adjustable to accommodate different limb sizes. The invention also relates to robotic exoskeletons having combinations of such features.

BACKGROUND OF THE INVENTION

Stroke, physical injury, and disease are causes of impairment of motor function involving one or more limbs. It is often possible to recover some motor function through rehabilitation, and practicing functional multi-joint movements with the impaired limb is an important part of motor recovery (Dobkin, 2004). Current therapeutic techniques therefore focus on training with repetitive, frequent functional movements (Teasell et al., 2003).

Providing patients with the attention they need is a challenge. Each patient requires extensive one-on-one attention, and therapy programs are physically exhausting for the therapist. The use of robotic devices to provide therapy would improve efficiency and effectiveness of the therapy, and this has been at the forefront of recent stroke rehabilitation research (Hesse et al., 2003; Reinkensmeyer et al., 2004). Robots not only have the ability to provide repetitive functional movement training, but also can provide sensitive and objective quantitative assessments of movement. The technology also makes it possible for a single therapist to supervise multiple patients simultaneously.

Existing robots for upper limb rehabilitation and assistance include MIT-MANUS (Krebs et al., 1998), MIME (Burgar et al., 2000), GENTLE/s (Loureiro et al., 2003), MULOS (Johnson et al., 2001), T-WREX (Sanchez et al., 2004; ARMEO (available from Hocoma AG, Switzerland); Sanchez et al., 2006), ARMin (Mihelj et al., 2006; Mihelj et al., 2007), and KINARM™ (Scott, 1999), among others. Exoskeleton robotic devices have the advantage of direct control over limb joint function, which allows independent control of each DOF of the limb. This ensures that compensatory movements by a subject can be monitored and/or prevented. A drawback of exoskeleton devices is that coupling of the robotic linkage to the subject's limb requires alignment of the axes of the limb joint and the corresponding robot joint. With current exoskeleton robots, this results in parts of the robot being located close to the subject, which may be intimidating to some subjects.

A further drawback of current robotic devices is that they cannot match the full mobility of the human upper limb. This is particularly true for the shoulder complex because it has a compact arrangement of five major degrees of freedom (DOF): two at the sternoclavicular joint and three at the glenohumeral joint. The glenohumeral joint can be approximated as a ball-and-socket joint and has been replicated in some current devices. However, the shoulder girdle has been neglected, despite its importance in stabilizing and orienting the upper limb. Without direct control at the sternoclavicular joint, it is not possible to prevent the subject from making compensatory movements, nor is there a way to properly regain strength and coordination of the shoulder girdle.

SUMMARY OF THE INVENTION

One aspect of the invention relates to a robotic exoskeleton, comprising: mechanical linkage that couples to a selected joint of a limb of a subject, the mechanical linkage including at least one joint having articulation about an axis; and limb attaching means for attaching the limb to the mechanical linkage; wherein mechanical linkage of the exoskeleton is not located on or along an axis of the selected joint of the limb.

The mechanical linkage may define a virtual joint at a point not located on the mechanical linkage; and the virtual joint may be coupled to the selected joint of the limb when the limb is attached to the mechanical linkage.

In one embodiment, the mechanical linkage may comprise a plurality of links interconnected for articulation therebetween so as to define two parallelogram structures, the two parallelogram structures sharing at least portions of two links, one said parallelogram having a virtual side defined between two corners, the two corners fixed to ground.

In another embodiment, the mechanical linkage may comprise two or more solid links and at least one cable.

In another embodiment, the mechanical linkage may comprise a curved track with a circular curvature; a carriage associated with the curved track; and one or more of: (i) two or more links interconnected for articulation therebetween and connected at one point to the carriage; (ii) at least one cable connected at one point to the carriage and at least at one point to the track; and (iii) means associated with the carriage for driving and/or resisting movement of the carriage on the track.

The mechanical linkage may further comprise at least one motor for moving the mechanical linkage and/or resisting movement of the mechanical linkage via the cables.

The robotic exoskeleton may couple first and second joints of the limb of the subject; wherein mechanical linkage of the exoskeleton is not located on or along an axis of the first joint of the limb. The exoskeleton may provide two degrees of freedom (DOF), one DOF for each of the first and second joints of the limb.

The robotic exoskeleton may couple to first, second, and third joints of the limb of the subject; wherein mechanical linkage of the exoskeleton is not located on or along an axis of the first joint of the limb. The robotic exoskeleton may provide three degrees of freedom (DOF), one DOF for each of the first, second, and third joints of the limb.

Articulation of the exoskeleton may be within a plane.

The limb may be an arm or a leg. The selected joint may be the sternoclavicular joint, the glenohumeral joint, the elbow, the wrist, the hip, the knee, or the ankle.

In another embodiment the exoskeleton couples to first, second, and third joints of the limb of the subject and provides up to six degrees of freedom (DOF), two DOF for the first joint of the limb, three DOF for the second joint of the limb, and one DOF for the third joint of the limb; wherein mechanical linkage of the exoskeleton is not located on or along one or more of the axes of the first joint of the limb. The exoskeleton may be adjusted for motion only within a plane.

In another embodiment, the exoskeleton couples to first, second, third, and fourth joints of the limb of the subject and provides two DOF for the first joint of the limb, three DOF for the second joint of the limb, and one or two DOF for the third joint of the limb, and one, two, or three DOF for the fourth joint of the limb; wherein mechanical linkage of the exoskeleton is not located on or along one or more of the axes of the first joint of the limb.

The limb may be the arm, wherein the first and second joints may be the sternoclavicular and the glenohumeral joints of the shoulder, and the third and fourth joints may be the elbow and the wrist.

The robotic exoskeleton may further comprise means for obtaining data respecting angular position, torque, and/or acceleration of at least one of the joints or the links of the mechanical linkage.

At least a portion of the mechanical linkage may be adjustable for limbs of different length; wherein the mechanical linkage is a closed loop structure so that links do not require length adjustment when the mechanical linkage is adjusted for limbs of different length.

Joints of the mechanical linkage may be coupled by cables; wherein the mechanical linkage is a closed loop structure so that cables do not require length and/or tension adjustment when the mechanical linkage is adjusted for limbs of different length.

According to a second aspect of the invention there is provided a method for assessing, studying, diagnosing a deficit in, and/or treating an impairment in motor function of a limb of a subject, comprising: coupling a selected joint of the limb about a particular axis to a mechanical linkage of a robotic exoskeleton; wherein mechanical linkage of the robotic exoskeleton is not located on or along the particular axis of the selected joint of the limb; and wherein articulation of the robotic exoskeleton is related to motor function of the selected joint of the limb.

The mechanical linkage may define a virtual joint at a point not located on the mechanical linkage; and coupling may include coupling the selected joint of the limb about a particular axis to the virtual joint of the mechanical linkage.

In one embodiment, coupling may include coupling first and second joints of the limb of the subject to the mechanical linkage; wherein mechanical linkage of the exoskeleton is not located on or along an axis of the first joint of the limb. The exoskeleton may provide two degrees of freedom (DOF), one DOF for each of the first and second joints of the limb.

In another embodiment, coupling may include coupling first, second, and third joints of the limb of the subject to the mechanical linkage; wherein mechanical linkage of the exoskeleton is not located on or along one or more of the axes of the first joint of the limb. The exoskeleton may provide three degrees of freedom (DOF), one DOF for each of the first, second, and third joints of the limb.

In another embodiment, coupling may include coupling first, second, and third joints of the limb and provides up to six degrees of freedom (DOF), two DOF for the first joint of the limb, three DOF for the second joint of the limb, and one DOF for the third joint of the limb; wherein mechanical linkage of the exoskeleton is not located on or along one or more of the axes of the first joint of the limb.

Investigating may comprise obtaining data respecting angular position, torque, and/or acceleration of at least one joint or link of the mechanical linkage, the data corresponding to angular position, torque, and/or acceleration of one or more joints of the limb.

Another aspect of the invention relates to a robotic exoskeleton, comprising: a first mechanical linkage that couples to a first selected joint of a limb of a subject, the first mechanical linkage including links for said coupling to the first selected joint, with at least one joint having articulation about an axis; and limb attaching means for attaching the limb to the linkage; wherein the first mechanical linkage defines a virtual joint having an axis that is not located on the mechanical linkage; wherein the virtual joint is coupled to the first selected joint of the limb when the limb is attached to the linkage; and wherein the first mechanical linkage is not located on or along an axis of the coupled first selected joint of the limb.

The first mechanical linkage may comprise a plurality of links interconnected for articulation therebetween so as to define two four-bar structures, the two four-bar structures sharing at least portions of two links, one said four bar structure having a virtual link defined between two corners, the two corners fixed to ground. At least one of the four-bar structures may be a parallelogram.

In some embodiments, the first mechanical linkage may comprise two or more links and at least one cable. In another embodiment, the first mechanical linkage may comprise: a curved track; a carriage associated with the curved track; and two or more links interconnected for articulation therebetween and connected at one point to the carriage and at another point to a fixed location relative to the curved track.

The robotic exoskeleton may further comprise at least one motor for moving the first mechanical linkage and/or resisting movement of the first mechanical linkage.

The robotic exoskeleton may further comprise: a second mechanical linkage that couples to a second selected joint of the limb of the subject, the second mechanical linkage including links for said coupling to the second selected joint, with at least one joint having articulation about an axis; wherein a joint of the second mechanical linkage is located on or along an axis of the second selected joint of the limb.

In one embodiment the first mechanical linkage may comprise a plurality of links interconnected for articulation therebetween so as to define at least one four-bar structure; and the second mechanical linkage comprises a plurality of links interconnected for articulation therebetween. In another embodiment, the plurality of links may define at least one parallelogram structure.

One or more links of the first mechanical linkage may be shared with one or more links of the second mechanical linkage. The first mechanical linkage may comprise a curved track, a carriage associated with the curved track, and two or more links interconnected for articulation therebetween and connected at one point to the carriage and at another point to a fixed location relative to the curved track; and the second mechanical linkage comprises a plurality of links interconnected with pulleys and cables for articulation therebetween. Articulation of the exoskeleton may be within a plane.

The robotic exoskeleton may further comprise: a third mechanical linkage that couples to a third selected joint of the limb of the subject, the third mechanical linkage including links for said coupling to the third selected joint, with at least one joint having articulation about an axis; wherein a joint of the third mechanical linkage is located on or along an axis of the third selected joint of the limb.

Two or more of the first mechanical linkage, the second mechanical linkage, and the third mechanical linkage may share one or more links. The first mechanical linkage may comprise a curved track, a carriage associated with the curved track, and two or more links interconnected for articulation therebetween and connected at one point to the carriage and at another point to a fixed location relative to the curved track; the second mechanical linkage may comprise a plurality of links interconnected with pulleys and cables for articulation therebetween; and the third mechanical linkage may comprise a plurality of links interconnected with pulleys and cables for articulation therebetween. Articulation of the exoskeleton may be within a plane.

The robotic exoskeleton may further comprise: a second mechanical linkage that couples to the first selected joint of the limb of the subject, the first and second mechanical linkages providing two degrees of freedom to the first selected joint; or a second mechanical linkage that couples to the first selected joint of the limb of the subject, and a third mechanical linkage that couples to the first selected joint of the limb of the subject, the first, second, and third mechanical linkages providing three degrees of freedom to the first selected joint; wherein the second mechanical linkage includes links for said coupling to the first selected joint and having articulation about an axis that corresponds to a second axis of rotation of the first selected joint of the limb; and wherein the third mechanical linkage includes links for said coupling to the first selected joint and having articulation about an axis that corresponds to a third axis of rotation of the first selected joint of the limb.

The robotic exoskeleton may further comprise one of:

(i) a third mechanical linkage that couples to a second selected joint of the limb of the subject;

(ii) a third mechanical linkage that couples to a second selected joint of the limb of the subject and a fourth mechanical linkage that couples to the second selected joint of the limb of the subject, the third and fourth mechanical linkages providing two degrees of freedom to the second selected joint; and (iii) a third mechanical linkage that couples to a second selected joint of the limb of the subject, a fourth mechanical linkage that couples to the second selected joint of the limb of the subject, and a fifth mechanical linkage that couples to the second selected joint of the limb of the subject, the third, fourth, and fifth mechanical linkages providing three degrees of freedom to the second selected joint;

wherein the second mechanical linkage includes links for said coupling to the first selected joint and having articulation about an axis that corresponds to a second axis of rotation of the first selected joint of the limb;

wherein the third mechanical linkage includes links for said coupling to the second selected joint and having articulation about an axis that corresponds to a first axis of rotation of the second selected joint of the limb;

wherein the fourth mechanical linkage includes links for said coupling to the second selected joint and having articulation about an axis that corresponds to a second axis of rotation of the second selected joint of the limb; and wherein the fifth mechanical linkage includes links for said coupling to the second selected joint and having articulation about an axis that corresponds to a third axis of rotation of the second selected joint of the limb.

The robotic exoskeleton may further comprise: a sixth mechanical linkage that couples to a third selected joint of the limb of the subject; wherein the sixth mechanical linkage includes links for said coupling to the third selected joint and having articulation about an axis that corresponds to an axis of rotation of the third selected joint of the limb.

In the above embodiments at least one of the first mechanical linkage, the second mechanical linkage, the third mechanical linkage, the fourth mechanical linkage, and the fifth mechanical linkage may comprise a curved track, a carriage associated with the curved track, and two or more links interconnected for articulation therebetween and connected at one point to the carriage and at another point to a fixed location relative to the curved track. Two or more of the first mechanical linkage, the second mechanical linkage, the third mechanical linkage, the fourth mechanical linkage, and the fifth mechanical linkage may share one or more links.

The robotic exoskeleton of any of the above embodiments may further comprise means for obtaining data respecting angular position, torque, and/or acceleration of at least one of the joints or the links of the mechanical linkage.

The robotic exoskeleton of any of the above embodiments may be configured for motion only within a plane.

In another embodiment the robotic exoskeleton may comprise: a first mechanical linkage that couples to a first selected joint of a limb of a subject, the first mechanical linkage including at least two links for said coupling to the first selected joint and having articulation about a first axis that corresponds to an axis of rotation of the first selected joint of the limb; and limb attaching means for attaching the limb to the linkage; wherein the first axis of rotation of the first mechanical linkage is substantially collinear with the axis of rotation of the first selected joint of the limb; wherein a second axis of rotation of the first mechanical linkage is substantially collinear with an axis of rotation of a second selected joint of the limb, the second selected joint of the limb being the next joint which is distal or proximal to the first selected joint of the limb; and wherein a distance between the first and second axes of rotation of the first mechanical linkage is variable and proper performance of the mechanical linkage is maintained without adjusting length of links of the mechanical linkage.

In another embodiment the robotic exoskeleton may comprise: the mechanical linkage described above for coupling to a first selected joint of a limb; and a second mechanical linkage that couples to a second selected joint of the limb of the subject, the second mechanical linkage including at least two links for said coupling to the second selected joint and having articulation about a second axis that corresponds to an axis of rotation of the second selected joint of the limb; wherein the second axis of rotation of the second mechanical linkage is substantially collinear with the axis of rotation of the second selected joint of the limb; wherein a third axis of rotation of the second mechanical linkage is substantially collinear with an axis of rotation of a third selected joint of the limb, the third selected joint of the limb being the next joint which is distal or proximal to the second selected joint of the limb; and wherein a distance between the second and third axes of rotation of the second mechanical linkage is variable and proper performance of the second mechanical linkage is maintained without adjusting length of links of the second mechanical linkage.

Another aspect of the invention relates to a method for assessing, studying, diagnosing a deficit, and/or treating an impairment in sensorimotor function of a limb of a subject, comprising: coupling a first mechanical linkage to a first selected joint of a limb of a subject, the first mechanical linkage including links for said coupling to the first selected joint, with at least one joint having articulation about an axis; obtaining data relating to angular position, torque, and/or acceleration of at least one joint or link of the mechanical linkage, the data corresponding to angular position, torque, and/or acceleration of one or more joints of the limb; and using the data to assess, study, diagnose a deficit, and/or treat an impairment in sensorimotor function; wherein the first mechanical linkage defines a virtual joint having an axis that is not located on the mechanical linkage; wherein the virtual joint is coupled to the first selected joint of the limb; and wherein the first mechanical linkage is not located on or along an axis of the coupled first selected joint of the limb.

The method may further comprise: coupling a second mechanical linkage to a second selected joint of the limb, the second mechanical linkage including links for said coupling to the second selected joint, with at least one joint having articulation about an axis; wherein a joint of the second mechanical linkage is located on or along an axis of the second selected joint of the limb.

The method may further comprise: coupling a third mechanical linkage to a third selected joint of the limb, the third mechanical linkage including links for said coupling to the third selected joint, with at least one joint having articulation about an axis; wherein a joint of the third mechanical linkage is located on or along an axis of the third selected joint of the limb.

The method may further comprise: coupling a second mechanical linkage to the first selected joint of the limb, the first and second mechanical linkages providing two degrees of freedom to the first selected joint; or coupling a second mechanical linkage and a third mechanical linkage to the first selected joint of the limb, the first, second, and third mechanical linkages providing three degrees of freedom to the first selected joint; wherein the second mechanical linkage includes links for said coupling to the first selected joint and having articulation about an axis that corresponds to a second axis of rotation of the first selected joint of the limb; and wherein the third mechanical linkage includes links for said coupling to the first selected joint and having articulation about an axis that corresponds to a third axis of rotation of the first selected joint of the limb.

The method may further comprise one of: (i) coupling a third mechanical linkage to a second selected joint of the limb of the subject; (ii) coupling a third mechanical linkage to a second selected joint of the limb of the subject and coupling a fourth mechanical linkage to the second selected joint of the limb of the subject, the third and fourth mechanical linkages providing two degrees of freedom to the second selected joint; and (iii) coupling a third mechanical linkage to a second selected joint of the limb of the subject, coupling a fourth mechanical linkage to the second selected joint of the limb of the subject, and coupling a fifth mechanical linkage to the second selected joint of the limb of the subject, the third, fourth, and fifth mechanical linkages providing three degrees of freedom to the second selected joint; wherein the second mechanical linkage includes links for said coupling to the first selected joint and having articulation about an axis that corresponds to a second axis of rotation of the first selected joint of the limb; wherein the third mechanical linkage includes links for said coupling to the second selected joint and having articulation about an axis that corresponds to a first axis of rotation of the second selected joint of the limb; wherein the fourth mechanical linkage includes links for said coupling to the second selected joint and having articulation about an axis that corresponds to a second axis of rotation of the second selected joint of the limb; and wherein the fifth mechanical linkage includes links for said coupling to the second selected joint and having articulation about an axis that corresponds to a third axis of rotation of the second selected joint of the limb.

Another aspect of the invention relates to a method for assessing, studying, diagnosing a deficit, and/or treating an impairment in sensorimotor function of a limb of a subject, comprising: coupling a first mechanical linkage to a first selected joint of a limb of a subject, the first mechanical linkage including at least two links for said coupling to the first selected joint and having articulation about a first axis that corresponds to an axis of rotation of the first selected joint of the limb; obtaining data relating to angular position, torque, and/or acceleration of at least one joint or link of the mechanical linkage, the data corresponding to angular position, torque, and/or acceleration of one or more joints of the limb; and using the data to assess, study, diagnose a deficit, and/or treat an impairment in sensorimotor function; wherein the first axis of rotation of the first mechanical linkage is substantially collinear with the axis of rotation of the first selected joint of the limb; wherein a second axis of rotation of the first mechanical linkage is substantially collinear with an axis of rotation of a second selected joint of the limb, the second selected joint of the limb being the next joint which is distal or proximal to the first selected joint of the limb; and wherein a distance between the first and second axes of rotation of the first mechanical linkage is variable and proper performance of the mechanical linkage is maintained without adjusting length of links of the mechanical linkage.

BRIEF DESCRIPTION OF THE DRAWINGS

For a more detailed understanding of the invention, and to show more clearly how it may be carried into effect, the invention will be described, by way of example, with reference to the accompanying drawings, wherein:

FIG. 6a shows how the mechanical linkage behaves as the arm position changes. FIG. 6b shows alternative embodiment in which links of the exoskeleton have been replaced with cables and pulleys.

FIGS. 8a to 8c show embodiments of a planar robotic exoskeleton attached to an arm, viewed from below, based on a combination of the embodiments shown in FIGS. 1a and 6a.

In these figures, the shoulder joint is mechanically coupled off-axis and the elbow is also mechanically coupled. FIG. 8a shows the embodiments of FIGS. 1a and 6a combined without modification. FIG. 8b shows the embodiment of FIGS. 1a and 6a combined, but using fewer links than the embodiment of FIG. 8a. FIG. 8c shows how the parallelograms of the embodiment of FIG. 6a are defined in the embodiment of FIG. 8b.

FIG. 9a shows the exoskeleton with a closed-loop cable-drive system, and FIG. 9b shows the same exoskeleton driven by an open-loop cable-drive system.

FIG. 13a illustrates the reaching task setup. FIG. 13b shows the recorded hand paths of the subject. FIG. 13c shows the individual joint motion of the three joints during one of the movements: the shoulder, the elbow and the wrist.

DETAILED DESCRIPTION OF ILLUSTRATIVE EMBODIMENTS

Figure 1A:
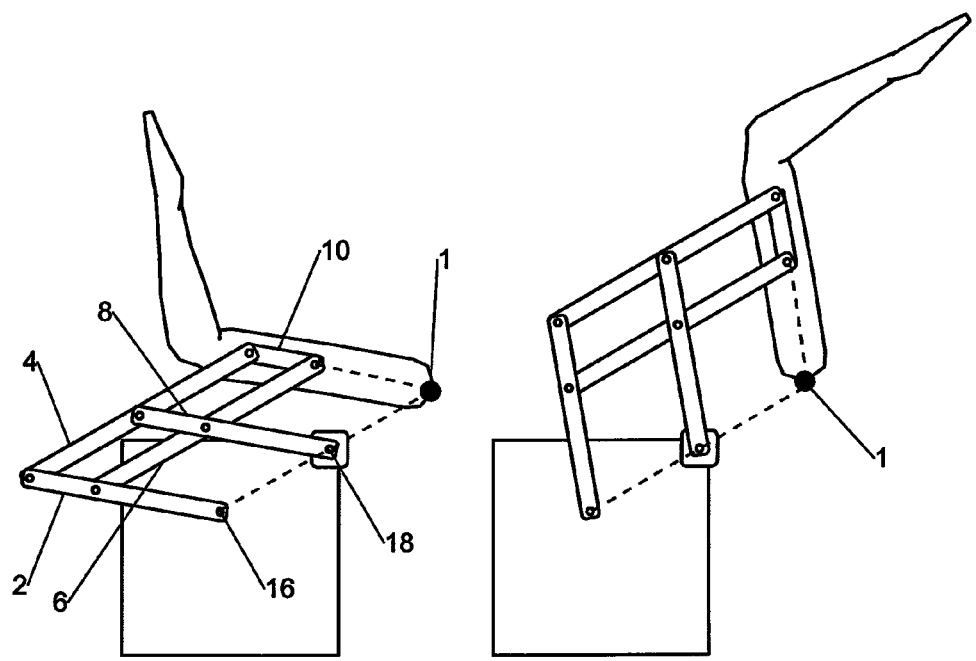
FIGS. 1a and 1b are diagrams of an embodiment of a planar robotic exoskeleton attached to an arm, viewed from below, in which links of the exoskeleton form two parallelogram structures (shown darkened in FIG. 1b), and the shoulder joint is mechanically coupled off-axis.

Impaired sensorimotor function of one or more of a subject's limbs may be caused by stroke, physical injury (i.e., trauma), or disease, and combinations of these. Research in areas such as sensorimotor function in normal and impaired individuals, and diagnosing, assessing and/or treating (i.e., rehabilitation, therapy) of sensorimotor function in individuals with such impairments may advantageously employ a robotic device.

As used herein, the term "limb" refers to a limb, or portion thereof, and may refer to either an upper limb or a lower limb.

One aspect of the invention relates to a robotic exoskeleton for use with a subject's limb. The robotic exoskeleton includes a mechanical linkage (also referred to herein as a "linkage") having links or segments connected at articulating joints. The limb, which may be an upper or lower limb, and which may or may not be impaired, is attached to the exoskeleton. Attaching the limb to the exoskeleton couples one or more joints of the limb to one or more joints of the mechanical linkage. Sensors (e.g., encoders, torque sensors, accelerometers) for obtaining data relating to position, angle, acceleration, force (e.g., torque), etc., of one or more joints and/or segments the limb may be deployed on and/or associated with the mechanical linkage of the exoskeleton.

Another aspect of the invention relates to assessing and/or rehabilitating and/or studying sensorimotor function of a subject with impaired motor function. The subject, whose limb is attached to the exoskeleton, may be instructed to carry out one or more tasks, or the limb may be guided through one or more tasks by the robotic exoskeleton. Encoders may be mounted on and/or associated with the joints and/or segments of the exoskeleton to provide accurate joint angle measurements and to enhance position control performance. Data relating to movement of the limb may be collected during such tasks. Such data may relate to position, angle, acceleration, force (e.g., torque), etc., of one or more joints and/or segments of a limb.

A robotic exoskeleton according to the invention may also be used in research applications to study sensorimotor function and/or proprioception (i.e., position sense and kinesthesia) in individuals. For example, the robotic exoskeleton may be used to investigate how sensory information respecting a limb is used for a broad range of sensory and motor functions. The robotic exoskeleton may be useful for obtaining such data from normal, healthy individuals, and also from individuals with brain injury and/or neurological disorders in which such sensorimotor and/or proprioception are impaired, as it may aid one or more of assessment, diagnosis, treatment, management, and therapy for such individuals. Use of the robotic exoskeleton with subjects/limbs not having impaired sensorimotor function may provide control data.

For the case where a joint of a limb has only one axis of rotation, the term "coupling" as used herein refers to the joining of a joint of the mechanical linkage of the exoskeleton to a joint of the limb. Such joining of joints occurs when the kinematics and kinetics about one axis of each of the two joints are related, meaning that motion or torque about an axis at one joint will produce a related motion or torque about an axis of the other joint. Depending on the mechanism of coupling, the motion (or torque) between the coupled joints may be related linearly (e.g., one-to-one), proportionally, or in some other predictable relationship. The axis of the joint of the limb and the axis of the joint of the mechanical linkage may or may not be substantially aligned (e.g., coaxial, or collinear). If the axes are aligned, this will be referred to herein as collinear coupling. If they are not aligned, this will be referred to herein as remote coupling. Remote coupling may be achieved off-axis, wherein none of the mechanical linkage or other parts of the exoskeleton is located on or along the axis of the selected joint of the limb. Remote coupling may also be achieved on-axis, wherein part of the mechanical linkage and/or other part of the exoskeleton is located on or along the axis of the selected joint of the limb. The term "coupling" may also refer to the joining of a first joint of the mechanical linkage to a second joint of the mechanical linkage.

When a joint of a limb has two or more degrees of freedom, the limb joint may be represented by two or more axes of rotation that intersect at the centre of rotation of the limb joint. These axes may be referred to as limb joint axes. The centre of rotation of the limb may also be referred to as the limb joint centre. For the case where a joint of a limb has two or more axes of rotation, the term "coupling" as used herein refers to the joining of a joint of the mechanical linkage of the exoskeleton to a limb joint axis. An example of this is provided in section 4.

As used herein, the term "ground" is intended to mean a point, relative to the robotic exoskeleton, to which a portion or joint of the mechanical linkage is fixedly attached. The ground may be referred to as a reference point. The ground may be established on part of the chassis or framework associated with the robotic exoskeleton.

As used herein, the term "collinear" is intended to mean lying on the same straight line.

Whereas the below embodiments are described with respect to the joints of the upper limb, it will be appreciated that the embodiments may be configured for use with other joints, such as, for example, the hip, knee, etc., and may have N degrees of freedom (i.e., single DOF, two DOF, three DOF, etc.). According to the embodiments described herein, information, data, the execution of tasks, etc., relating to the multiple joints of a limb may be obtained/carried out independently and/or simultaneously for the joints concerned.

Insofar as the terms "first", "second", "third", etc., are used herein with respect to joints of a mechanical linkage or joints of a limb, such use shall not be construed as implying any anatomical relationship between the joints, or a consecutive order of the joints. For example, a "first" joint is not to be construed as being more proximal or more distal to the body than a "second" joint or a "third" joint. Rather, such use of "first", "second", "third", etc., is intended to distinguish among multiple joints of a mechanical linkage or of a limb, as the case may be.

1 Off-Axis Remote Coupling to a Joint of a Limb Via a Virtual Joint of a Mechanical Linkage In one embodiment, the invention relates to a robotic exoskeleton including a mechanical linkage having articulation about a plurality of joints, wherein the articulation defines a virtual joint of the mechanical linkage. As used herein, the term "virtual joint" refers to a point not located on the mechanical linkage that would form a joint if two or more links were extended so as to intersect at that point. When attached to a subject's limb, the mechanical linkage provides coupling of the virtual joint to a selected joint of the limb such that there is no mechanical linkage or other parts of the exoskeleton located on or along the axis of the selected joint of the limb. Such coupling of a joint of a limb is referred to herein as off-axis remote coupling. For example, the vertical axis of the glenohumeral joint runs through the body, and is close to the head above the shoulder; however, a robotic linkage according to this embodiment of the invention may be coupled to this joint about the vertical axis without placing any of the mechanical linkage substantially above or below the shoulder. Among the advantages of this approach is the fact that the motors used to drive the robotic linkage are no longer required to be located above the shoulder, adjacent to the subject's head, as they were in prior robotic devices (see, for example, U.S. Pat. No. 6,155,993, issued Dec. 5, 2000 to Scott). Rather, this embodiment allows the driving motors to be located below the mechanical linkage and away from the subject, which increases the subject's comfort. It will of course be appreciated that the approach described herein that permits such alignment may be generalized to other limbs/joints of the body, such as the sternoclavicular joint, hip, knee, etc.

Two examples of mechanical linkages that may be used to achieve off-axis remote coupling according to the invention are described below.

1.1 Two-Parallelogram Mechanical Linkage

Figure 1B:
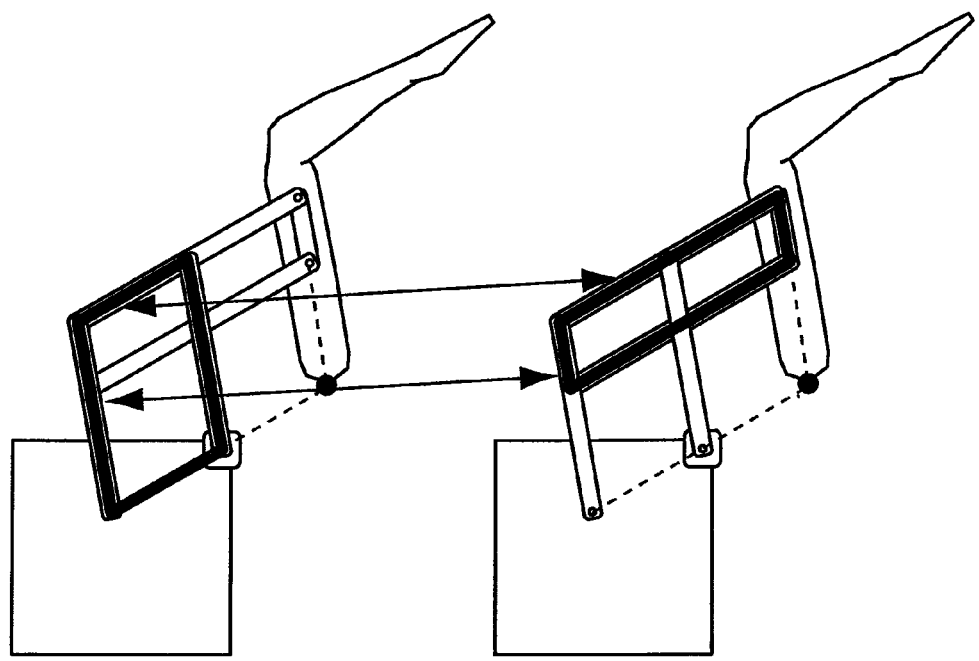
Figure 1C:
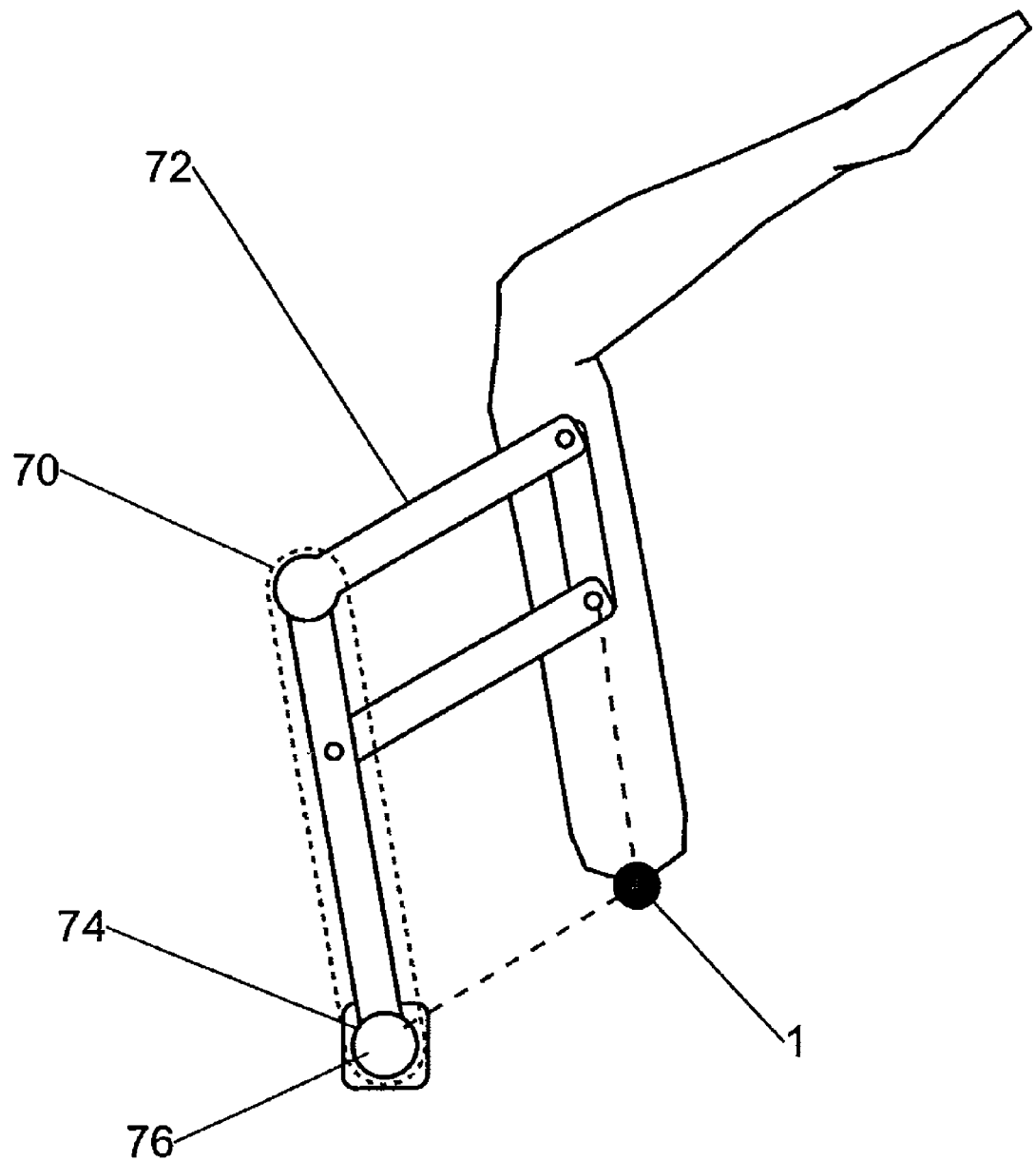
FIG. 1c shows an alternative embodiment in which links of the exoskeleton have been replaced with cables and pulleys.

FIGS. 1a and 1b show an example of a planar exoskeleton attached to an arm, viewed from below, in which the shoulder joint is remotely coupled off-axis to the virtual joint of the mechanical linkage defined at the point indicated by reference numeral 1. As used herein, "planar" is intended to mean that articulation of the exoskeleton is limited to a space which may be defined by two coordinates (i.e., a plane). The plane may be oriented in any direction (e.g., horizontally, vertically, or any direction therebetween). This embodiment includes a six-link mechanical linkage, in which the links 2, 4, 6, 8, 10, and a virtual link between fixed points 16 and 18 define two parallelograms as shown in FIG. 1b. The two parallelograms share two sides, with one end of link 2 fixed to ground at 16 and having rotation about an axis defined at 16. Link 8 may be connected to a driving motor and/or encoder 18, which is also connected to ground. A driving motor and/or encoder may also be placed at 16 instead of 18. FIG. 1a shows how the mechanical linkage behaves as the shoulder joint angle is changed, and FIG. 1b shows the two shared links of the two parallelograms (which are links 2 and 4 in this figure; see arrows). It should be noted that the two shared links do not have to be the two indicated, as other pairs are possible. In this embodiment, the virtual joint 1 of the linkage is collinearly coupled to the shoulder joint. Joints 16 and 18, where a motor and/or encoder may be placed, are remotely coupled off-axis to the limb joint. The parallelograms may at least partially be implemented using cables and pulleys, as shown in FIG. 1c. In FIG. 1c, a pulley 70 is fixed to link 72, and another pulley 74 is fixed to ground at 76, and a cable is shown by the small dashes.

1.2 Curved Track Mechanical Linkage

Figure 2A:
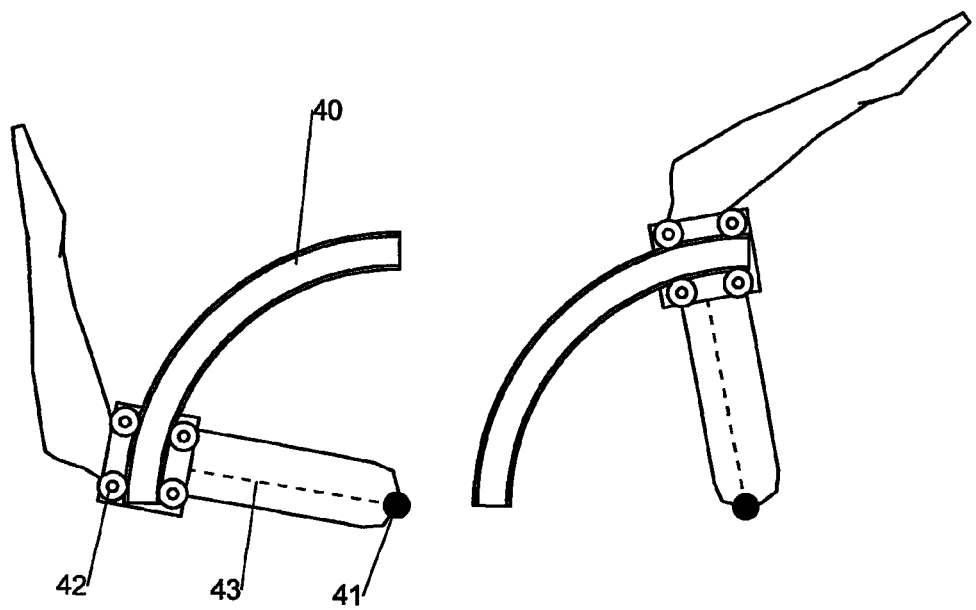
FIGS. 2a and 2b show embodiments of an exoskeleton including a curved track mechanical linkage.

FIG. 2a shows another embodiment of a robotic exoskeleton that provides off-axis remote coupling of a joint of a limb such as, in this case, the shoulder. Two shoulder positions are shown. Like the embodiment of FIGS. 1a to 1c, articulation of this embodiment is also planar. The mechanical linkage of this embodiment includes a rail or track 40, which supports and guides a carriage 42 through a circular range of motion. In this embodiment the curved track 40 is of constant radius. A virtual joint of the mechanical linkage is defined at the point indicated by reference numeral 41. The curved track is collinear with the axis of the joint of interest (in this case, the shoulder), and it thus forces the carriage to be aligned with the shoulder joint axis at any location on the track.

There are several ways to drive the carriage on a curved track. Previous examples indicate that the carriage may be driven directly by a motor mounted on the carriage wherein the motor is geared to the track (see, for example, U.S. Patent Publication No. 2003/0115954 A1, published on Jun. 26, 2003, to Zemlyakov and McDonough). There are also several cable (or belt) driven implementations in which a cable (or a belt) is routed along the curved track across the carriage. The cable (or belt) is fixed to each end of the track, and around an actuated shaft that is not collinear with the track. Rotation of the shaft has the end result of pulling the carriage along the track or moving the track relative to the carriage (see for example Nef et al., 2005; Mihelj et al., 2007; Frisoli et al., 2005; Perry et al., 2006, and also U.S. Patent Publication No. 2008/0009771 A1, published on Jan. 10, 2008, to Perry and Rosen). Typically, the actuator that drives this motion is attached to the carriage, so the actuator moves along with the carriage, but the actuator can be remotely located using cables.

Figure 2B:
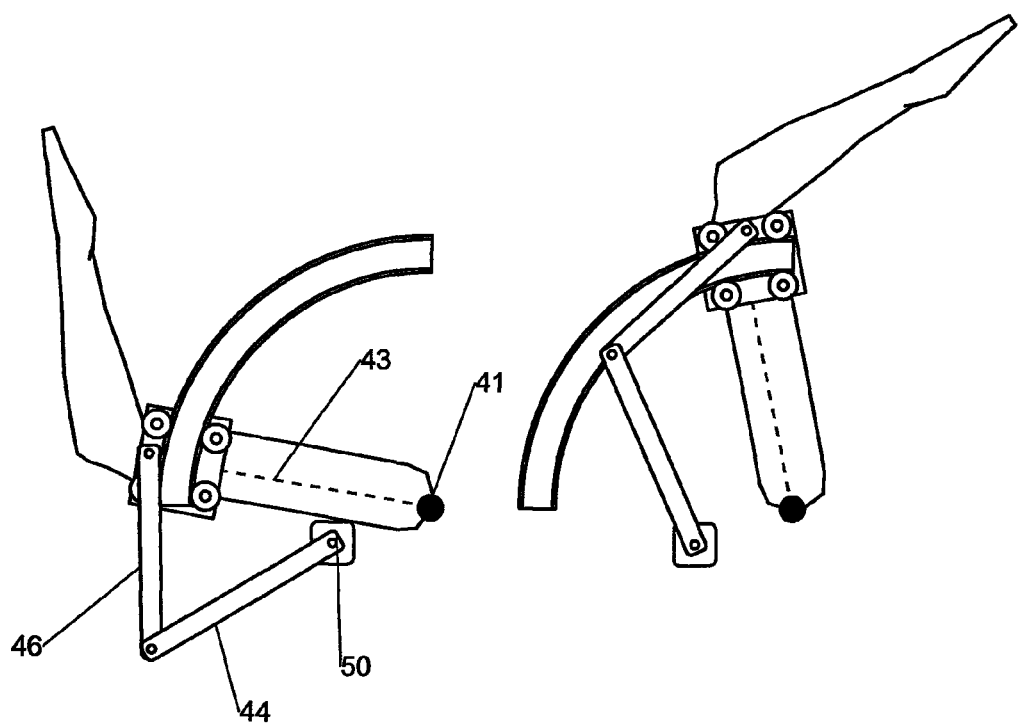

In the embodiment shown in FIG. 2b, the carriage is driven by links 44 and 46, where link 44 may be connected to one or more driving motors. A four-bar mechanical linkage is formed by links 44, 46, the virtual link 43, and the (fixed) link joining 50 and the shoulder joint axis 41, and in this case, the structure does not form a parallelogram, although it could, depending on its configuration. A parallelogram has the advantage of providing a simple, linear relationship between the motion (and torque) of joint 50 and the motion (and torque) of joint 41. The mechanical linkage including links 44, 46 is supported at joint 50, and by the carriage 42. It will be appreciated that because this mechanical linkage may be supported at both its proximal end (e.g., at joint 50) and at the track 40, it avoids some of the problems associated with compliance (i.e., movement of the mechanical linkage in a direction out of the plane). Compliance can be a problem for robotic exoskeletons that are supported only at one end. In addition, when configured for use with the subject's arm, all parts of the exoskeleton may be located away from the subject's head, either behind the subject or under the arm. This contributes to a more pleasant experience for the subject.

In the embodiment shown in FIG. 2b, the linkage coupled to the carriage has low compliance. In contrast, the previous designs described above use gears or cables which suffer from compliance and backlash. Also, in FIG. 2b, the carriage is directly coupled to joint 50 which has a fixed position relative to the track. This means that the actuator coupled to the carriage does not move along with the carriage. This reduces the inertia of the linkage substantially.

It should be noted that mechanical coupling of the carriage using links 44 and 46 may also be accomplished using cables (e.g., one cable pulling for extension, one for flexion) or some other type of actuation about joint 50.

1.3 Off-Axis Remote Coupling to a Joint of a Limb that has a Translational Component.

The approach described above for off-axis remote coupling between the exoskeleton and a limb joint may be extended to more complex situations. For example, there may be translation of a limb joint's axis of rotation during joint articulation, such that the position of the joint's instantaneous axis of rotation varies depending on the joint angle. An example of this situation is the knee joint (Zatsiosky, 1998). In this case, the off-axis remote coupling mechanisms described in Sections 1.1 and 1.2 may be adapted to capture this complexity by guiding the virtual joint along a prescribed trajectory that matches the trajectory of the instantaneous axis of rotation of the limb joint as the limb joint angle changes.

Figure 3A:
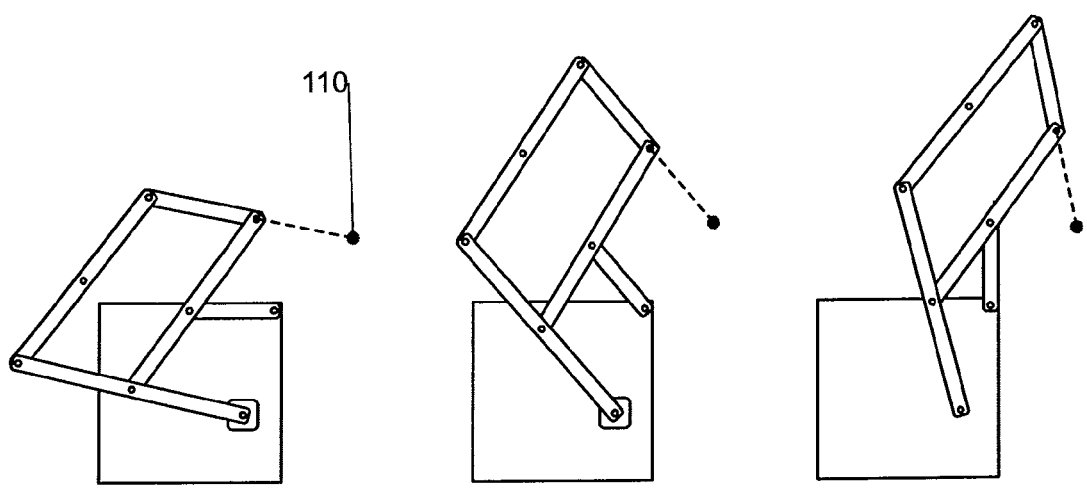
FIG. 3a shows an embodiment of FIG. 1a in which the parallelograms are replaced by four-bar structures that are not parallelograms.
Figure 3B:
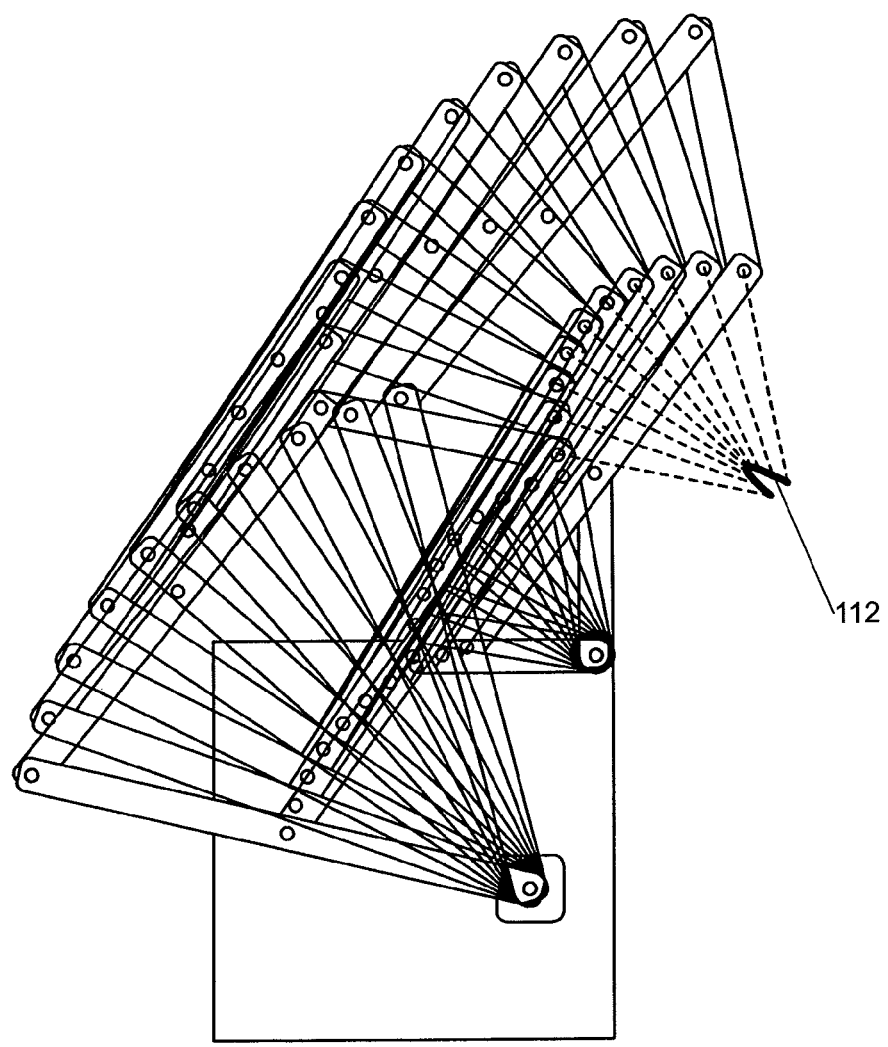
FIG. 3b shows that the linkage of FIG. 3a off-axis remote couples to a virtual joint axis that follows a prescribed trajectory.

For example, the embodiments of FIGS. 1a to 1c may be modified by replacing one or both of the two parallelograms with four-bar structures that are not parallelograms. In such an embodiment, the instantaneous virtual joint axis will move along a well-defined trajectory. The embodiment of FIG. 3a illustrates an example of off-axis remote coupling to a virtual joint 110, where both parallelograms are four-bar linkages that are not parallelograms. FIG. 3b shows multiple instances of the embodiment of FIG. 3a superimposed, as the linkage is stepped through a motion. The dashed lines indicate the virtual link at each step, and the thick line 112 joining the end-points of the dashed lines traces the trajectory of the instantaneous virtual joint axis. In this example, it is apparent that the steps in the middle of the motion primarily exhibit rotation (with little or no translation), while the steps at the beginning and end of the motion exhibit relatively more translation. Changing the lengths of the links in the mechanical linkage, the location of the linkage joints, and/or the position of the fixed corners of the linkage changes the shape of the trajectory of the instantaneous virtual joint axis, including the relative combination of rotation and translation.

Figure 4A:
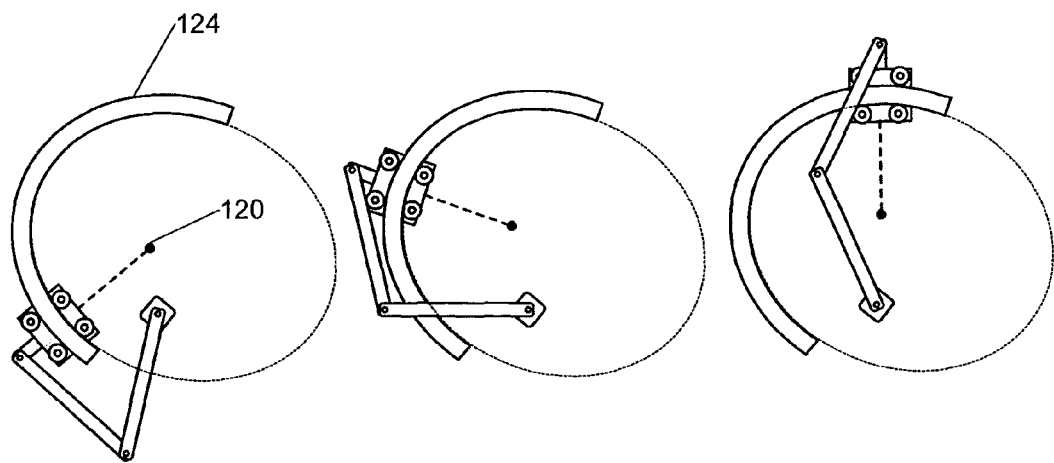
FIG. 4a shows an embodiment of FIG. 2b in which the curved track is replaced by a track with varying radius.
Figure 4B:
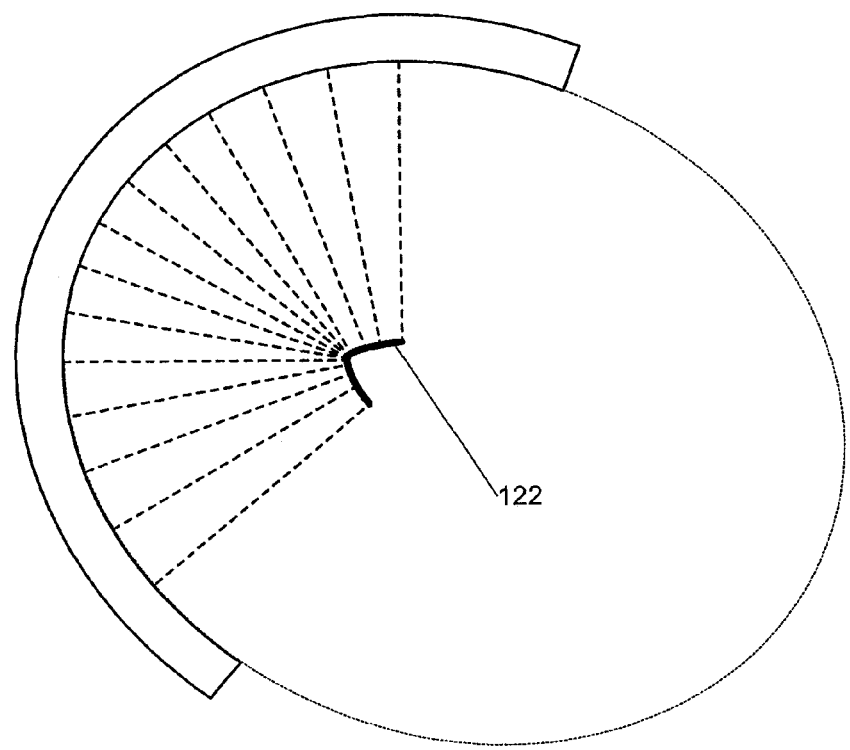
FIG. 4b shows that the linkage of FIG. 4a off-axis remote couples to a virtual joint axis that follows a prescribed trajectory.

In another example, the embodiment of FIG. 2b may be modified to replace the curved track of constant radius with a curved track of varying radius. In such an embodiment, the instantaneous virtual joint axis defined by the track will be constrained to a well-defined trajectory. The embodiment of FIG. 4a illustrates off-axis remote coupling of a virtual joint 120 for an elliptical track 124 (although the track may be any desired curvature). FIG. 4b shows the location of the virtual link (dashed lines) as the linkage is stepped through a motion. The thick line 122 joining the end-points of the dashed lines traces the trajectory of the instantaneous virtual joint axis. It is apparent that the steps in the middle of the motion primarily exhibit rotation (with little or no translation), while the steps at the beginning and end of the motion exhibit relatively more translation. Changing the curvature of the track changes the shape of the trajectory of the instantaneous virtual joint axis, including the relative combination of rotation and translation.

Figure 5A:
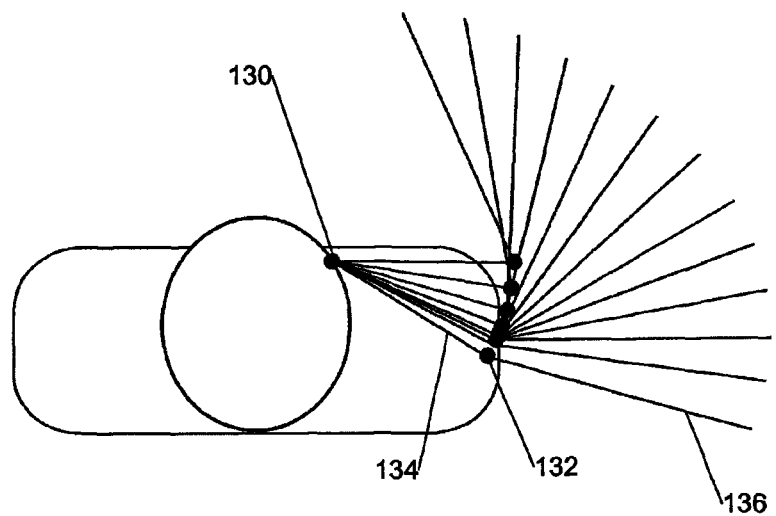
FIG. 5a shows a schematic of the naturally coupled motion of the sternoclavicular and glenohumeral joints of the right arm during a horizontal reaching movement, viewed from above.
Figure 5B:
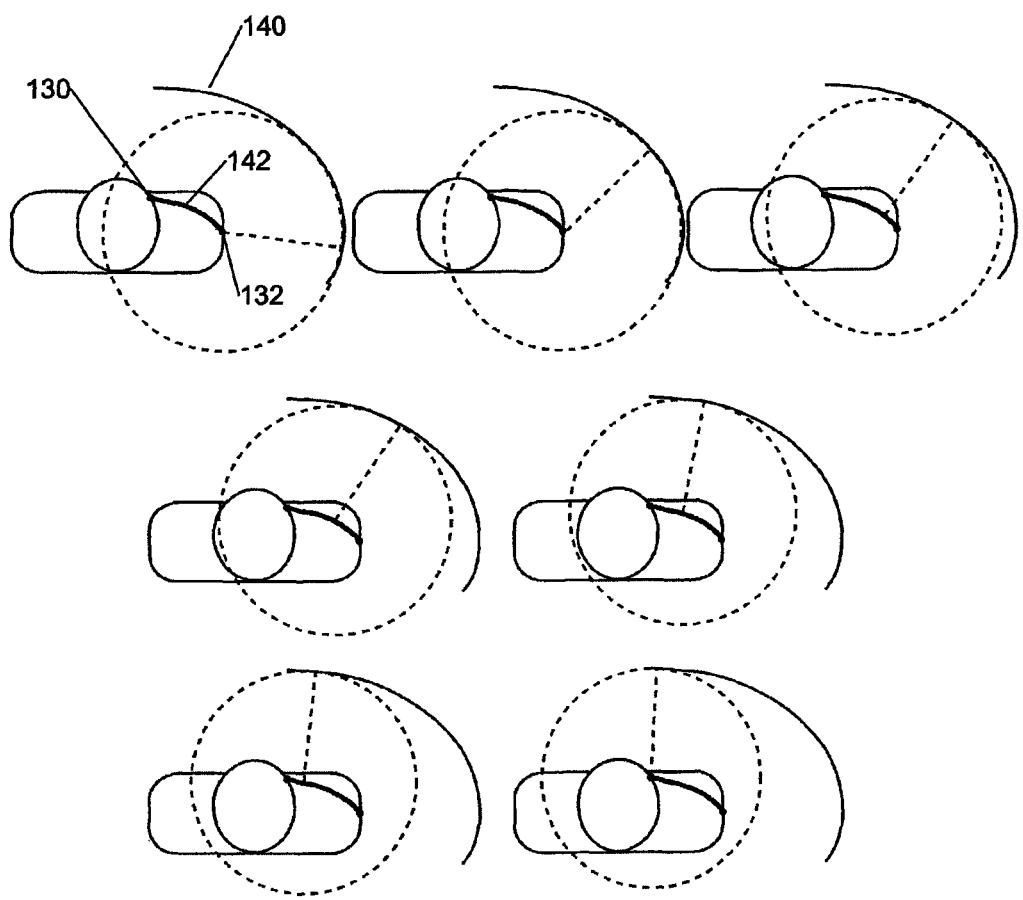
FIG. 5b shows how the instantaneous centre of rotation of the combined two-joint system (sternoclavicular and glenohumeral joints) moves during a reaching movement.

A second situation to which the embodiments in FIGS. 3a and/or 4a may be applied is in an exoskeleton that captures the motion of more than one joint. For example, there is a natural dependence between motion of the glenohumeral and sternoclavicular joints of the shoulder during reaching. FIG. 5a is a top view schematic of the right limb sternoclavicular joint 130 and the glenohumeral joint 132, where the clavicle is shown by lines 134, and the humerus is shown by lines 136 as the aim makes a planar reaching movement. For sideways reaches, the sternoclavicular joint does not contribute much to the overall shoulder motion. When a reach is made in front of the torso, the sternoclavicular joint contributes more to the motion. Similarly, the sternoclavicular joint contributes more to the motion as the reach is made backwards. The two joints have a natural coupling which can be described by a single virtual instantaneous axis of rotation. During parts of the motion that are primarily due to the glenohumeral joint, the virtual instantaneous axis of rotation will be substantially collinear with the glenohumeral joint axis. During parts of the motion that are primarily due to the sternoclavicular joint, the virtual instantaneous axis of rotation will be substantially collinear with the sternoclavicular joint axis. During parts of the motion that are a combination of glenohumeral and sternoclavicular motion, the virtual instantaneous axis of rotation will exist somewhere between the glenohumeral and sternoclavicular joint axes. This is shown schematically in FIG. 5b. The variable radius path 140 is a trace of the end of the humerus in FIG. 5a. The virtual instantaneous axis of rotation at a given point on 140 is located at the centre of the circle that defines the curvature at that point. The thick line 142 is a trace of the path that the virtual instantaneous axis of rotation follows during the reaching movement. Seven points along the path are shown in FIG. 5b. The trajectory 142 of the virtual instantaneous axis of rotation of this two joint system may be substantially mimicked using a mechanical linkage according to the embodiment illustrated in FIG. 3a, or using a curved track with varying radius as shown in the embodiment of FIG. 4a.

2 On-Axis Remote Coupling of a Joint, while Accommodating Various Limb Sizes

The problem being addressed by the embodiments in this section is how to on-axis remotely couple a limb joint while accommodating subjects of varying sizes, without having to modify the lengths of any of the linkage's structure beyond those that passively parallel the limb's geometry (i.e., for interface purposes). For example, in the KINARM (Scott, 1999), the KINARM's upper arm length must be adjusted for interface purposes to accommodate subjects of varying sizes. In addition, the KINARM's coupler link must also be adjusted in length (the KINARM's coupler link is part of the mechanical linkage that on-axis remotely couples the elbow joint). The below embodiments provide mechanisms whereby, for example, the KINARM's upper arm length would be the only part of the linkage requiring adjustment for subjects of varying sizes.

In one embodiment, a robotic exoskeleton includes a mechanical linkage having articulation about a plurality of joints, wherein a first joint of the mechanical linkage is on-axis remotely coupled to a second joint, which is either a limb joint or another linkage joint that is substantially collinear with a limb joint. The following constraints also apply:
(i) The distance between the coupled joints is adjustable and/or variable
(ii) For limb segments that are between the second coupled joint and either the first coupled joint or ground, at least one of the distances between adjacent limb joints is adjustable (e.g. for subjects of varying size);
(iii) That portion of the mechanical linkage that provides the coupling mechanism between the coupled joints is comprised of fixed-length links.

In another embodiment, a robotic exoskeleton includes a mechanical linkage having articulation about a plurality of joints, wherein an axis of one joint of the mechanical linkage is coupled to another joint of the linkage. Such coupling may be achieved between any two joints of the mechanical linkage that do not have collinear axes, and in which the one joint (hereafter referred to as the second coupled joint) is located on a mechanical linkage having N joints, where (N≥2), and the other joint (hereafter referred to as the first coupled joint) is located either on ground or on the same linkage. In some instances the first coupled joint may also be referred to as the driving joint, and the second coupled joint may also be referred to as the on-axis remote joint. The distance between the second coupled joint and the first coupled joint may be adjustable and/or variable, and the mechanical linkage may also have one or more of the following constraints:
(a) For joints of the mechanical linkage that are between the second coupled joint and the first coupled joint or ground, one of the distances between adjacent joints is adjustable (i.e., one of the links has a length that can be adjusted);
(b) the axis of the first coupled joint is not collinear with any of the joint axes of the mechanical linkage;
(c) the second coupled joint is the $n^{th}$ joint, where n≥4; or
(d) any combination of (a), (b), and/or (c).

2.1 Coupling within a Plane

Figure 6A:
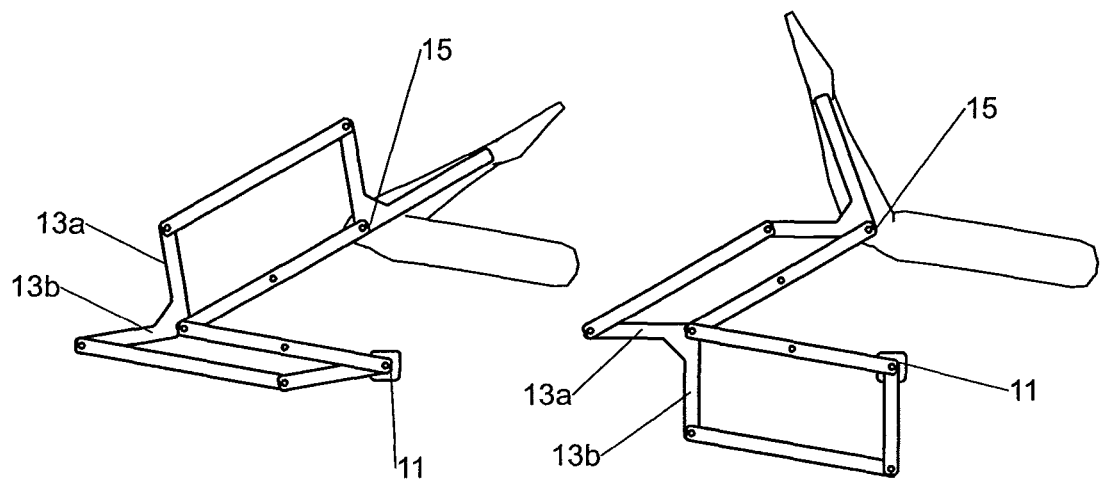
FIGS. 6a and 6b are diagrams of an embodiment of a planar robotic exoskeleton attached to an arm, viewed from below, in which the elbow joint is mechanically coupled.

FIG. 6a shows an embodiment of a two-parallelogram mechanical linkage of a robotic exoskeleton, which satisfies the constraints listed above. In this embodiment, as the elbow moves throughout space for a given subject, the distance between coupled joints is variable. The mechanical linkage is shown attached to an arm, in two arm positions. The first coupled joint of the mechanical linkage, indicated at 11, has its axis fixed to ground, and is also the point at which the mechanical linkage is connected to a driving motor (not shown). The second coupled joint, which is remotely coupled on-axis to the first coupled joint 11, is indicated at 15. As shown, the mechanical linkage provides on-axis remote coupling to the elbow. The driving motor at 11 for the mechanical linkage is not located on the axis of the elbow joint; however, the joint 15 of the exoskeleton is substantially coaxial with the elbow joint. Links 13a and 13b form a shared link between the two parallelograms, and they are rigidly joined together (e.g., they are made from a single piece of material) such that the angle between them does not change as the rest of the mechanical linkage changes. It will be appreciated that the coordinate frames of the two parallelograms of this embodiment are maintained in alignment (i.e., the coordinate frames do not rotate relative to one another) as the limb moves through different positions.

It is noted that the embodiment of FIG. 6a does not need to be adjusted for different elbow positions as the shoulder position moves or the shoulder rotates (i.e., because the parallelogram structure is maintained by default as the mechanical linkage changes position).

It will be appreciated that the two parallelograms shown in FIG. 6a may be replaced with any quadrilateral structures. However, the advantage of using a parallelogram-like structure, as shown in FIG. 6a, is that it is easier to resolve the kinetic and kinematic relationship between the driving joint of the mechanical linkage and the on-axis remotely coupled joint of the limb (i.e., angles, torques, etc. are equal at the two joints). The parallelograms may also be replaced with structures other than quadrilaterals (greater than 4 sides); however, structures having more links would have more degrees of freedom, which would require control.

Figure 6B:
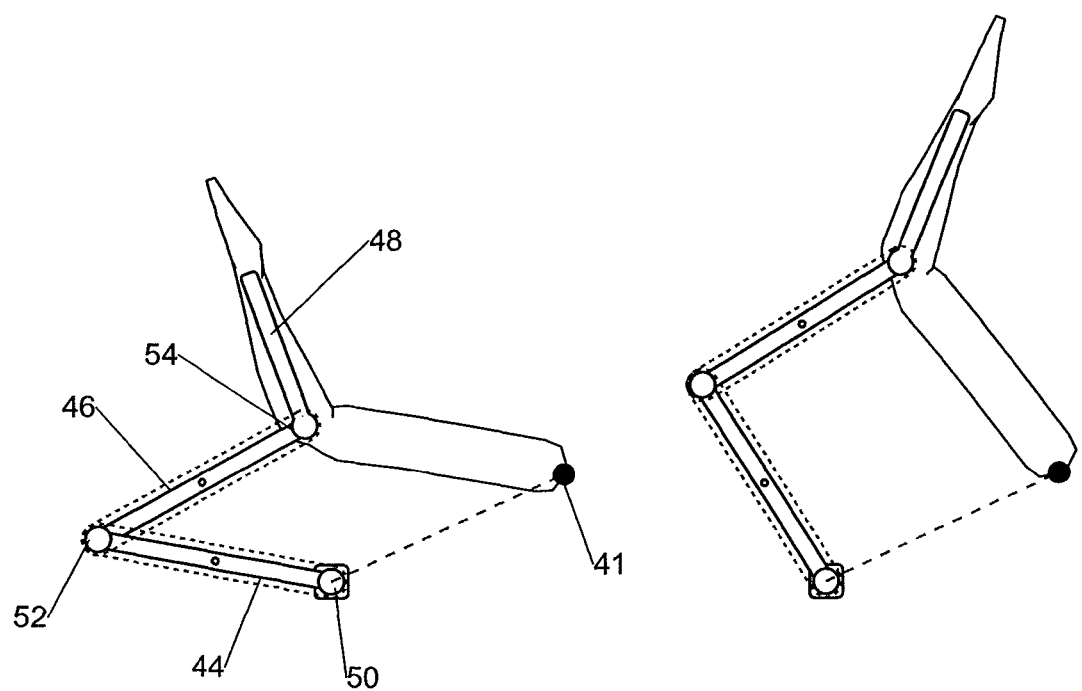

It will be appreciated that the two parallelograms defined by the links may also be formed using cables, as shown by small dashes in FIG. 6b. FIG. 6b also shows how the mechanism maintains on-axis remote coupling of the elbow joint as the shoulder joint is rotated. An example of such an embodiment is incorporated into the embodiments of FIGS. 9a and 9b (see section 3.2).

Figure 6C:
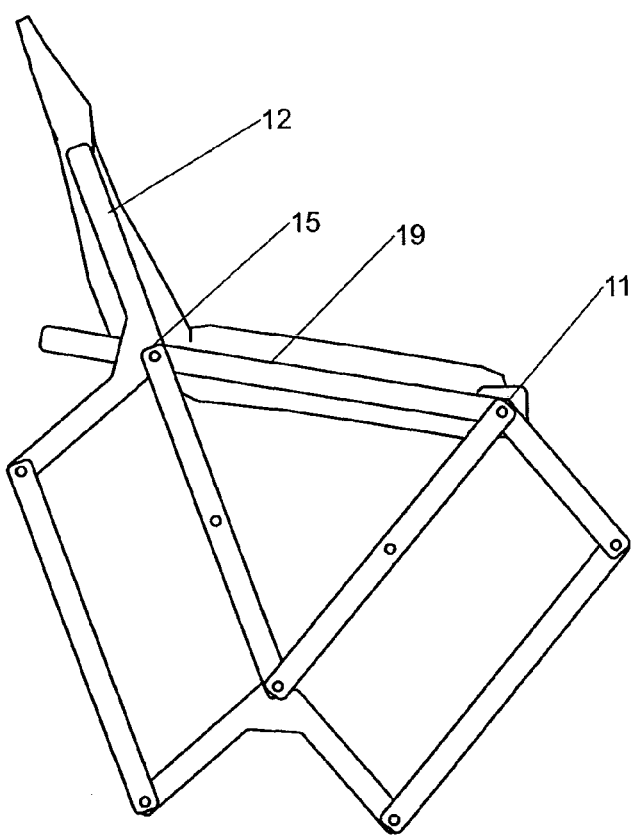
FIG. 6c shows an embodiment of the exoskeleton of FIG. 6a, in which link 19 has been added, and the axis of the joint 11 is fixed to ground and is collinear with the shoulder joint axis.
Figure 6D:
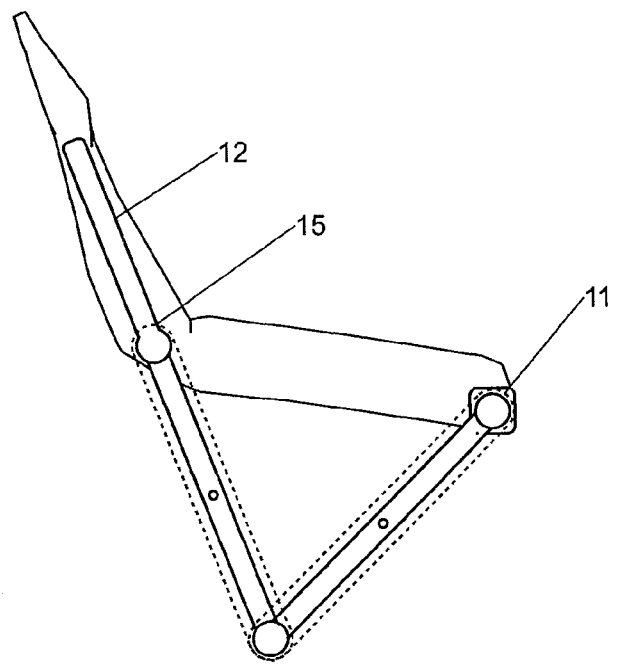
FIG. 6d shows an embodiment of FIG. 6c in which links of the exoskeleton have been replaced with cables and pulleys.

FIG. 6c shows an embodiment similar to that of FIG. 6a in which the ground joint 11 (i.e., the first coupled joint) is collinear with the shoulder joint. In addition, link 19, which is optional, has been added. Link 19 connects the two parallelograms between joints 15 and 11. Moreover, the connection of link 19 at joint 15 may be adjustable, so as to allow adjustment of the exoskeleton for different upper arm lengths. This embodiment provides an example in which the distance between coupled joints is constant for a given subject as the elbow moves throughout space, but is adjustable for subjects of different sizes. It is noted that the embodiment of FIG. 6c requires only a single adjustment at joint 15, which helps to maintain proper performance of the exoskeleton when adjusted for limbs of different subjects. That is, in the embodiment of FIG. 6c, when the mechanical linkage is adjusted for differences in upper arm length, there is no need to adjust the elbow mechanism links, because the parallelogram structure is maintained by default. In the embodiment of FIG. 6d, links of the embodiment of FIG. 6c have been replaced by cables and pulleys.

2.2 Coupling Out of the Plane

Figure 7:
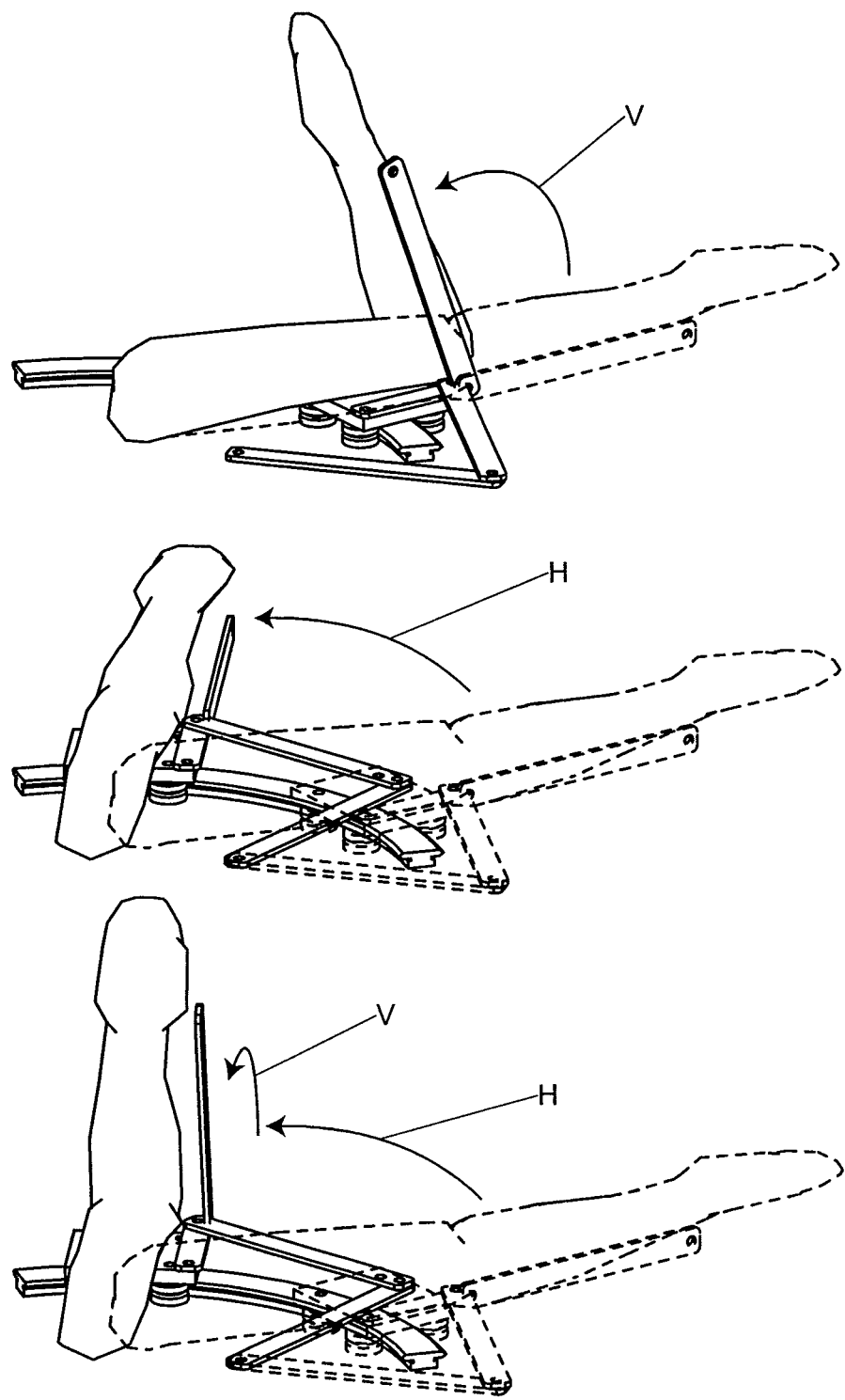
FIG. 7 shows an embodiment of a curved track mechanical linkage providing articulation of a limb out of the plane corresponding to the track.

It will be appreciated that it is not essential that the axes of the first and second coupled joints, about which coupling will occur, be parallel. For example, FIG. 7 shows an embodiment based on the curved track mechanical linkage of FIG. 2b, which provides articulation in a first plane indicated by arrow H and in a second plane indicted by arrow V. In this embodiment, the second coupled joint (the elbow) is coupled by a cable system (cables not shown). The cables form the equivalent of a two-parallelogram structure, but they may be guided in any direction so as to provide out-of-plane on-axis remote coupling.

3 Coupling of Two or More Joints of a Limb Wherein One Joint is Coupled Off-Axis The embodiments described above may be combined in various ways to provide a robotic linkage suitable for coupling to multiple joints of a limb for subjects of varying sizes. Examples of such embodiments are described below.

3.1 Parallelogram Mechanical Linkage

Figure 8A:
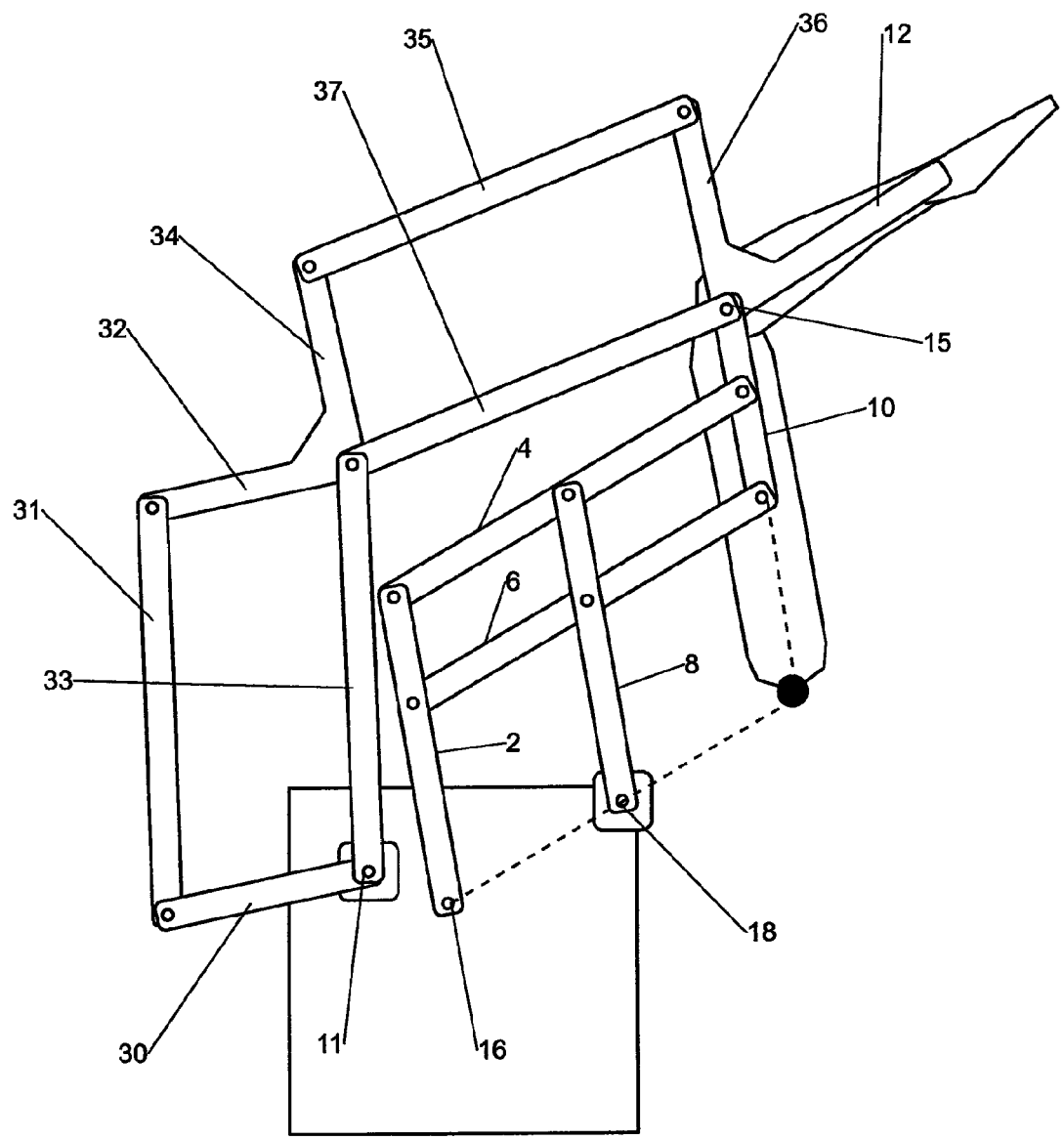

The embodiment of FIG. 1a provides a mechanical linkage for off-axis mechanical coupling of a joint of a limb. This embodiment may be combined with that of FIG. 6a to provide simultaneous off-axis remote coupling of a first joint of a limb and on-axis remote coupling of a second joint of a limb (or more generally, for any two joints of a limb). For example, FIG. 8a shows a bottom view of such an embodiment in which the mechanical linkages of FIGS. 1a and 6a are combined to provide a four parallelogram exoskeleton. That is, eight additional links 30 to 37 (32+34 and 36+12 are joined as rigid structures (i.e., at a fixed relative angle), such that the angle between them does not change as the rest of the mechanical linkage changes), are added to the embodiment of FIG. 1a to form two additional parallelogram structures. In the case of the arm, as shown, the shoulder joint is remotely coupled off-axis and the elbow is the second limb joint that is remotely coupled on-axis. In this embodiment, the axis about which ground joint 11 is remotely coupled on-axis to the joint 15 is not collinear with the axes of joints 16 or 18 of the mechanical linkage, and the linkage can be adjusted for differences in the distance between the second joint (elbow) and the first joint (shoulder) without altering the parallelogram structure of the on-axis remote joint (elbow) linkages or the parallelogram structure of the linkage providing off-axis remote coupling to the first joint (shoulder).

Figure 8B:
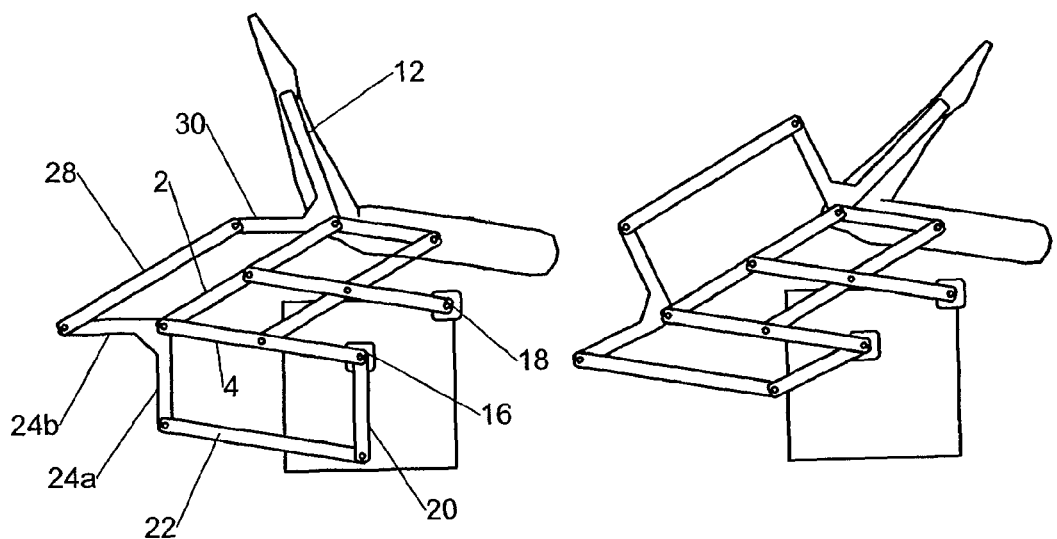
Figure 8C:
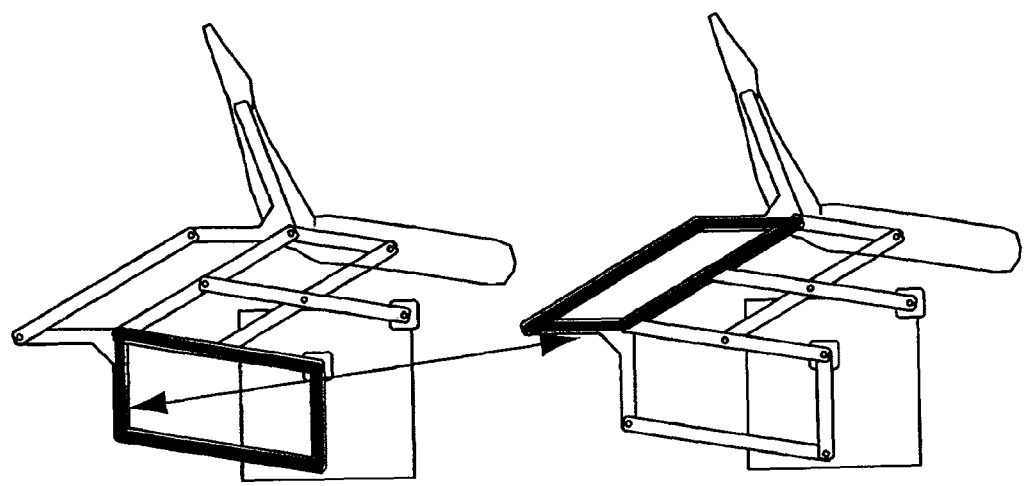

The embodiment shown in FIG. 8b is substantially the same as that of FIG. 8a, but is implemented with fewer links so as to simplify the exoskeleton. Links 20, 22, 24a+24b, 28, 30+12, 2, and 4 foam a seven-link, two-parallelogram structure, where links 24a+24b, and 30+12 are rigid structures (i.e., at a fixed relative angle), such that the angle between them does not change as the rest of the mechanical linkage changes. The mechanical linkage is shown in two positions corresponding to articulation of the forearm, showing how the mechanical linkage behaves as the on-axis remote joint (in this example, the elbow) angle is changed. Two of the four parallelograms, corresponding to the embodiment of FIG. 6a, are highlighted in FIG. 8c. In this embodiment, the ground joint 16 that is on-axis remotely coupled to the elbow joint is not aligned with the first joint 18 of the mechanical linkage. Two of the links 2 and 4 in the seven-link, two-parallelogram structure are shared with the links that drive the first joint 18, although this does not have to be the case (see below).

It is noted that in some embodiments, such as that shown in FIG. 8b, to adjust the mechanical linkage for the length of the limb (i.e., the upper arm), the shoulder linkage (i.e., the linkage corresponding to FIG. 1a) must be adjusted to maintain the parallelogram structure. Then the elbow linkage (i.e., links 2, 4, 20, 22, 24a, 24b, 28, 30, 12 of FIG. 8b) will no longer be a parallelogram structure, so this linkage must be adjusted accordingly. This is because links 2 and 4 are shared between the shoulder and elbow linkages. However, the embodiment of FIG. 8a simplifies the task of setting up the exoskeleton for limbs of different sizes, because the on-axis remote joint (elbow) linkage (i.e., links 30 to 37, 12 of FIG. 8a) does not need to be adjusted if the limb length changes. The mechanical linkage pertaining to the proximal (shoulder) joint (i.e., links 2, 4, 6, 8, 10 of FIG. 8a) also does not need to be adjusted if the limb length changes, because all that is required is to shift joint 15 along link 10. The reduced requirement to adjust the linkage for different sizes of limbs reduces the possibility of errors in performance of the exoskeleton which might arise from an improperly adjusted mechanical linkage.

For some prior devices, such as the robotic linkage disclosed in U.S. Pat. No. 6,155,993 which includes a single parallelogram, to adjust that mechanical linkage to a subject's elbow position, two links of the parallelogram need to be adjusted to precisely the same length to maintain the parallelogram structure and proper linkage performance. Thus, existing devices may be retrofitted with a mechanical linkage such as that shown in FIG. 6b to mechanically couple a remote (e.g., elbow) joint and simplify adjustment of the exoskeleton to different limb lengths.

3.2 Curved Track Mechanical Linkage, Two DOF

Figure 9A:
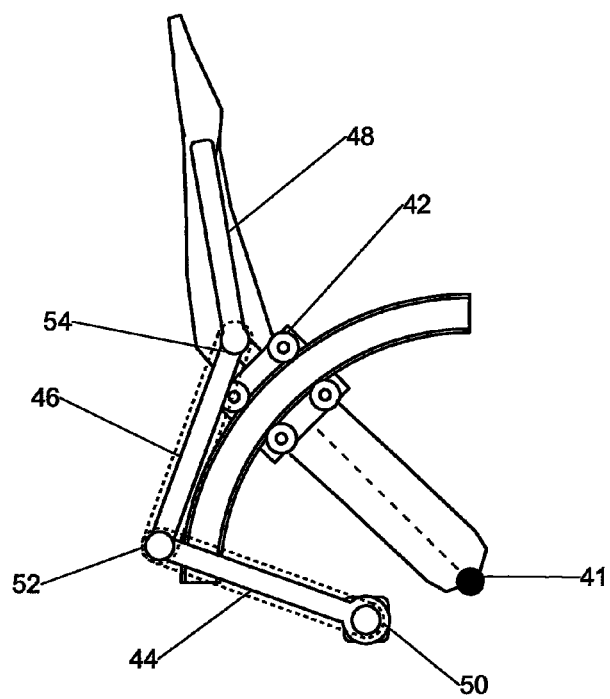
FIGS. 9a and 9b are diagrams of a planar robotic exoskeleton having 2 degrees of freedom and including a curved track and a carriage as part of its mechanical linkage. These embodiments combine the embodiments of FIGS. 2b and 6b.

The embodiment of FIG. 2a provides a mechanical linkage for off-axis remote coupling of a joint of limb. This embodiment may be combined with the embodiment of FIG. 6b to provide simultaneous off-axis remote coupling of one joint of a limb and on-axis remote coupling of another joint of the limb. FIG. 9 shows such an embodiment, providing two DOF of articulation: in the case of the arm, these correspond to one DOF at the shoulder and one DOF at the elbow. In the embodiment shown in FIG. 9a, one joint at 50 is used to provide off-axis remote coupling to joint 41 (the shoulder joint) as in the embodiment of FIG. 2b. This joint at 50 connects rigidly to link 44, and hence the carriage 42 is driven about the shoulder joint axis 41. A second joint at 50 is used to provide on-axis remote coupling to joint 54 (the elbow joint) as in the embodiment of FIG. 6b. This second joint at 50, which is not connected to link 44, connects to closed-loop cables (shown as small dashes) that on-axis remotely couple to joint 54, which is rigidly connected to link 48, so that the elbow joint is driven. The cables form the equivalent of a seven-link, two-parallelogram structure to drive the on-axis remote joint (elbow), and are connected to a motor. The motors driving both joints at 50 may also be back-driven by the mechanical linkage. Two of the links (44 and 46) in the 7-link, 2-parallelogram structure are shared with the links that couple the first joint (shoulder), although this does not have to be the case.

Figure 9B:
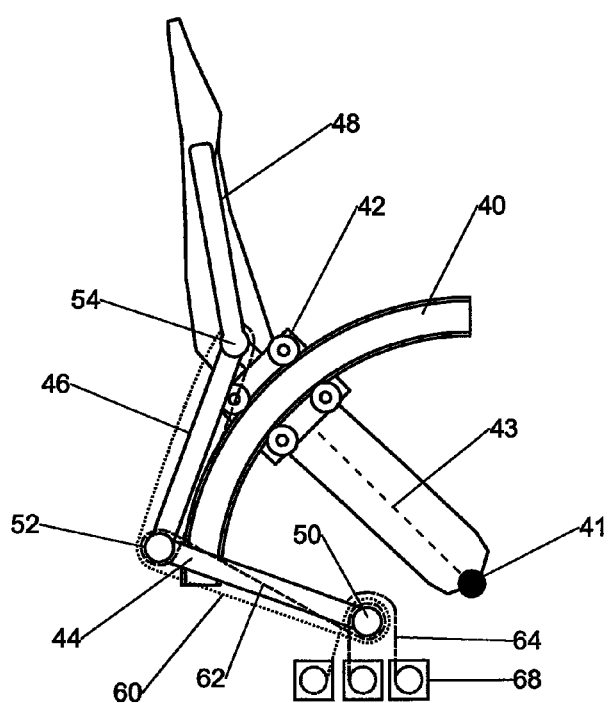

The embodiment of FIG. 9b shows the same off-axis and on-axis remote coupling as FIG. 9a, except that both joints at 50 are driven by an open-ended cable system. In this embodiment neither of the joints at 50 are rigidly connected to link 44. Three cables, 60, 62, and 64 are configured so that they act as a rigid connection to link 44 and as on-axis remote coupling to joint 54 by applying appropriate combinations of forces to the cables. This open-loop system drives both the shoulder and elbow joints, and the cables are connected to motors 68. The motors may also be back-driven by the mechanical linkage.

3.3 Curved Track Mechanical Linkage, Three DOF

Figure 10:
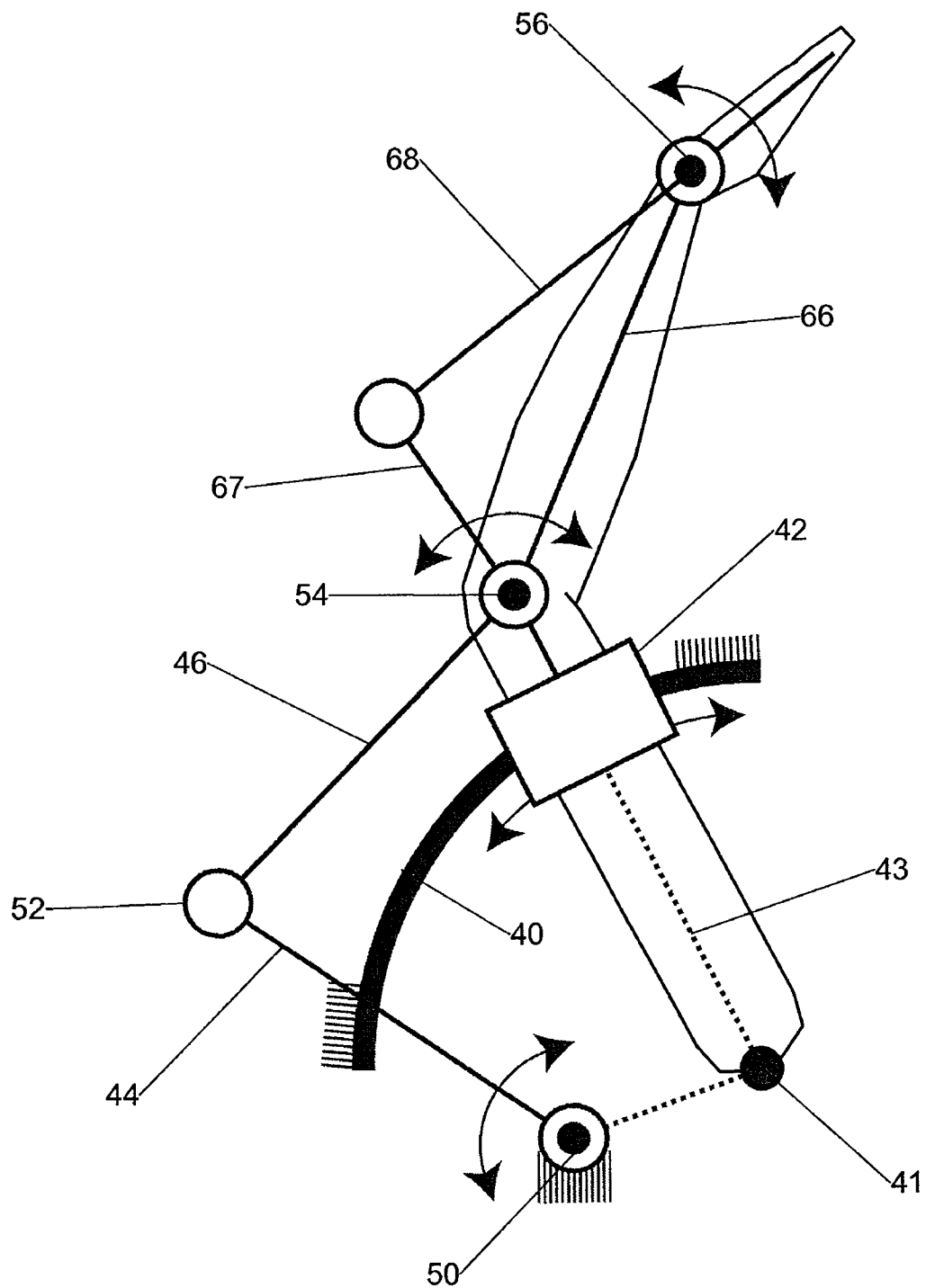
FIG. 10 is a diagram of a planar robotic exoskeleton having 3 degrees of freedom and including a curved track and a carriage as part of its mechanical linkage. This embodiment combines the embodiment of FIG. 9a (for shoulder and elbow) and a cable-driven version of the embodiment of FIG. 6c (for wrist).

As shown in FIG. 10, another embodiment provides a third DOF by addition of the joint 56. Where the arm is the limb of interest, and the first two joints are the shoulder and elbow, this third DOF corresponds to the wrist. This embodiment may be adapted for use with the leg, in which case the three DOFs correspond to the hip, knee, and ankle.

Figure 11A:
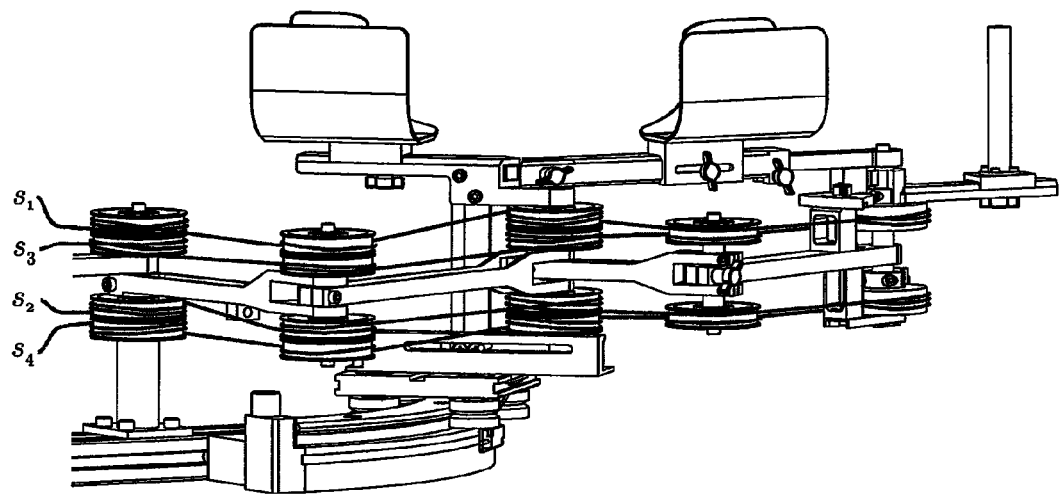
FIG. 11a is a drawing showing the cable routing scheme used for the planar robotic exoskeleton of FIG. 10.
Figure 12:
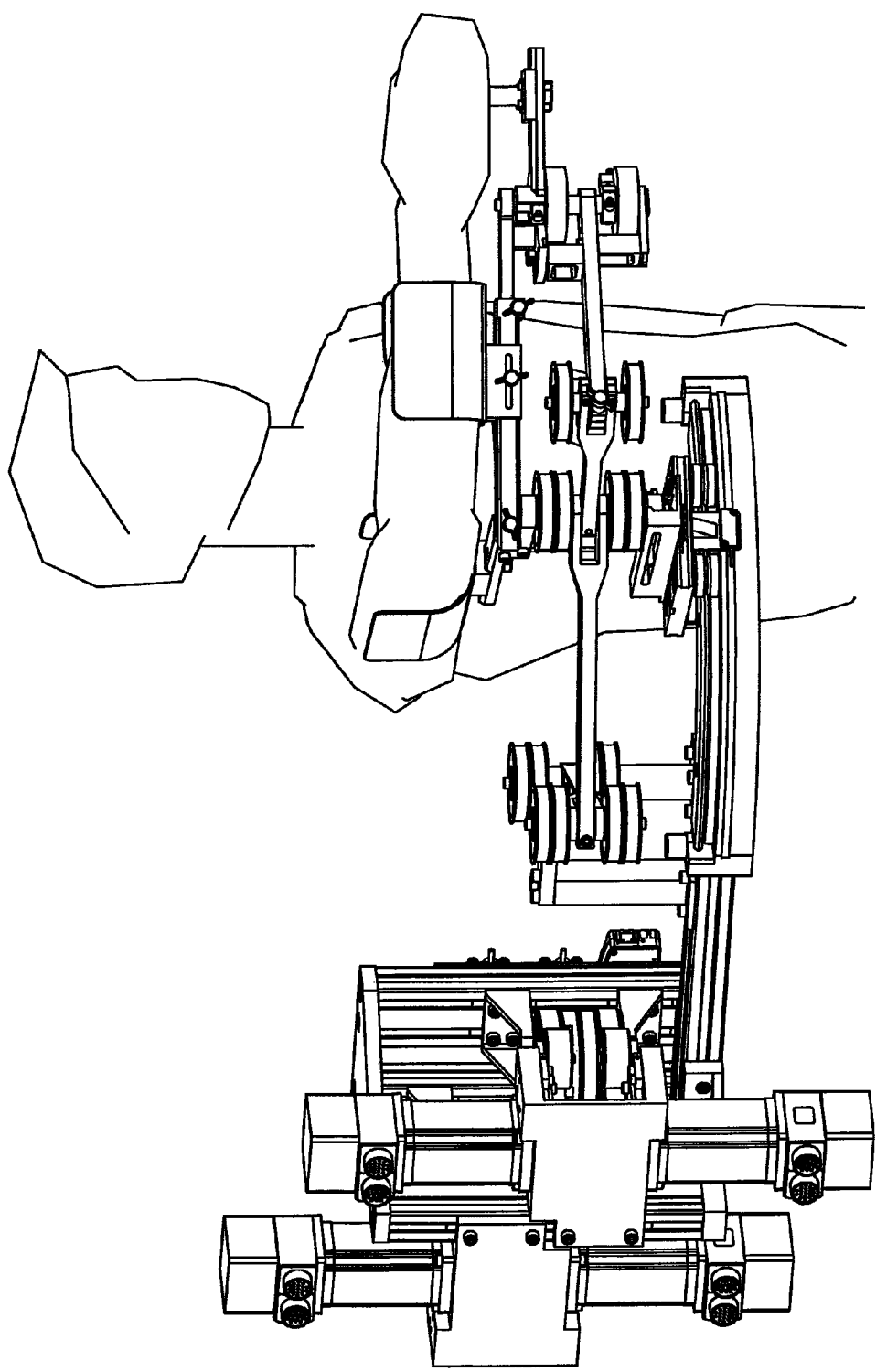
FIG. 12 is a drawing of the planar robotic exoskeleton of FIGS. 10, 11a, and 11b, shown in use (cables not shown).

The three DOF robotic exoskeleton shown in FIG. 11a and FIG. 12 was constructed based on the embodiment shown in FIG. 10. This embodiment combines a number of the previously described embodiments, including the embodiment of FIG. 9b for off-axis remote coupling of the shoulder joint and on-axis remote coupling of the elbow joint, plus an embodiment of FIGS. 6a and 6c to on-axis remotely couple the wrist joint. The joint 56 corresponding to the wrist is on-axis remotely coupled to a driving joint 54 corresponding to the elbow (via the linkage shown in FIG. 6c), and the driving joint 54 is on-axis remotely coupled to a driving joint 50 attached to ground via the linkage of FIG. 6a.

This embodiment thus extends one of the features of the embodiment of FIG. 6a, namely that a second coupled joint of a mechanical linkage (such as, for example, a joint corresponding to the elbow, relative to the shoulder) may be coupled to a third joint (such as, for example, a joint corresponding to the wrist, relative to the shoulder and elbow), so to as to provide an intermediate driving joint between two remotely coupled joints. That is, a remotely coupled (second) joint of a mechanical linkage may be used as a driving joint for a subsequent (third) coupled joint of the linkage.

Note that in the embodiment of FIG. 10, the lengths of virtual link 43 (upper arm) and link 66 (forearm) may be adjusted for different limb lengths without adjusting any of the other links in the mechanical linkage that provide the mechanical coupling (i.e. links 44, 46, 67, 68).

The hinged linkage 44, 46 driving the carriage 42 also serves to guide the cables along the mechanism. A second linkage 67, 68 guides the cables between elbow and wrist joints. These linkages ensure that tension is maintained in the cables when the length of the mechanism 66 is adjusted (e.g., for different limb lengths). All links may be machined from aluminum or other suitable material to keep the mass and inertial properties low. Each joint may be provided with a mechanical limit to prevent the exoskeleton's movements from extending beyond the safe limits of a subject's limb.

Figure 11B:
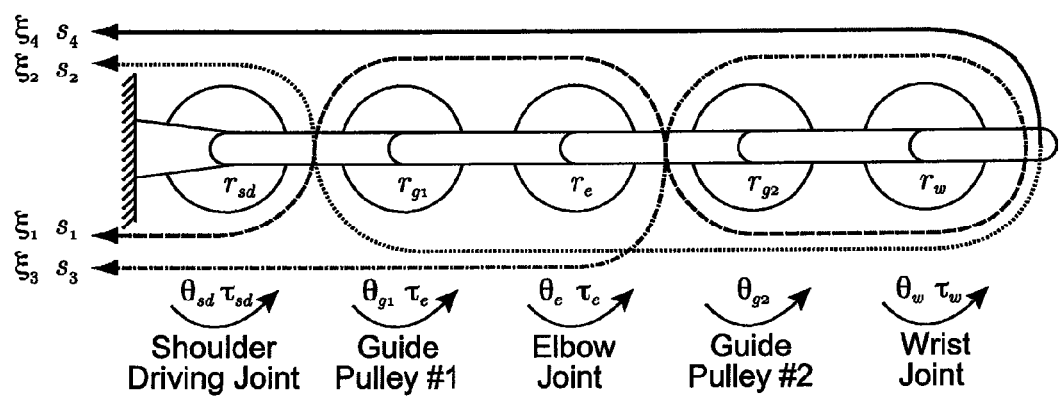
FIG. 11b is a simplified planar schematic representation of the optimal routing of the four cables. Symbols s, ξ, r, τ and θ represent cable displacement, cable force, pulley radius, joint torque, and joint angle, respectively.

In the embodiment shown in FIGS. 11a, 11b, and 12, all three DOFs may be actuated by an open-ended cable-drive system. Open-ended cable systems can apply force in one direction only, so it is necessary to have at least one more cable than DOF to achieve motion in both rotational directions at each joint. Thus four cables driven by electric motors are required to achieve full motion capability. It will be appreciated that a closed-loop cable-driven system may also be used for the embodiment shown in FIG. 10 in a manner analogous to that described for the two DOF curved track mechanical linkage (section 3.2).

As a consequence of the imbalance between the number of cables and DOF in open loop cable-drive systems, additional transformations are required to relate motion of the motors to motion at the joints. First of all, the cables span multiple joints, so motion and torque about a single joint is shared among the cables. Also, the position of the hinged linkage driving the carriage affects the length of the cables, and therefore must be included in the calculations. Overall, cable displacement, s, and joint angle, θ, are related using (1). Likewise, cable force, ξ, and joint torque, τ, are related using (2). These relationships are illustrated in FIG. 11b.

$$\begin{bmatrix} s_1 \\ s_2 \\ s_3 \\ s_4 \end{bmatrix} = \begin{bmatrix} -r_{sd} & r_e & -r_w & -1 \\ r_{sd} & -r_e & -r_w & 1 \\ -r_{sd} & -r_e & r_w & 1 \\ r_{sd} & r_e & r_w & -1 \end{bmatrix} \begin{bmatrix} \theta_{sd} \\ \theta_e \\ \theta_w \\ \theta_{hl} \end{bmatrix} \quad (1)$$

$$\begin{bmatrix} \tau_{sd} \\ \tau_e \\ \tau_w \end{bmatrix} = \begin{bmatrix} -r_{sd} & r_{sd} & -r_{sd} & r_{sd} \\ r_e & -r_e & -r_e & r_e \\ -r_w & -r_w & r_w & r_w \end{bmatrix} \begin{bmatrix} \xi_1 \\ \xi_2 \\ \xi_2 \\ \xi_4 \end{bmatrix} \quad (2)$$

Note the use of the subscript 'sd', which refers to the shoulder driving joint (i.e., joint 50), not the shoulder joint angle ($\theta_s$) (i.e., joint 41), which can be calculated using standard four-bar linkage relations. The contribution of the hinged linkage motion to the cable displacement is denoted by $\theta_{hl}$.

The choice of cable routing scheme for an open-ended cable-drive system has a significant effect on the performance of the exoskeleton. In theory, there are five unique cable routing schemes for a three DOF mechanical linkage (Lee, 1991). The schemes were analyzed using the method proposed by Lee (1991) to find the choice which has minimal antagonism between cables and hence the most even distribution of forces across the cables, and also has the lowest peak forces. FIG. 11b illustrates the optimal routing scheme for the three DOF embodiment.

The elbow and wrist joint locations are adjustable (as a result of utilization of the embodiments of FIGS. 6a to 6d) to accommodate subjects with different upper arm and forearm lengths. The elbow adjustment may be made by sliding the mechanism relative to the carriage. A single quick-release clamp may be used to clamp the mechanism in place, The forearm linkage may be telescopic and clamped by thumbscrews.

The subject is secured to the mechanism at the upper arm and forearm using arm troughs made of, e.g., molded fiberglass, which can be adjusted along the linkages. A handle may be provided for the subject to grasp. The troughs and the handle may be adjusted with a single thumb screw clamp. In addition to attaching the subject's arm to the exoskeleton, it is necessary to align the shoulder joint with the robot. This may be achieved simply through adjustment of the chair position.

3.3.1 Dynamic Model and Simulation

A dynamic model was created in MATLAB based on the robot toolbox (Corke, 1996). Simulations were used to select appropriate motors and cables, and to assist with structural design.

The model was defined as a standard rigid-body manipulator with negligible cable dynamics. Dynamic parameters of the exoskeleton were estimates from CAD drawings, and upper limb parameters were calculated from anthropometric data tables based on subject height and weight (Winter, 1990). The model first calculated the joint torques required to achieve a given trajectory. The cable forces required to generate these joint torques were then calculated using the torque resolver technique, which includes a pretension force to prevent the cables from becoming slack (Lee, 1991). All forces and non-axial moments at each joint were calculated to evaluate joint strength.

Simulations were performed for various reaching movements with a peak end-point velocity of 1.0 m/s. Movements included single-joint motion through each joint's full range, and a variety of multi-joint reaching movements. In all cases, anthropometric limb measurements were chosen to meet the maximum design requirements. Motors, gear ratios, cables and joint bearings were selected based on the results of these simulations. The overall torque capability of each joint of the exoskeleton with a gear ratio of 3 for each motor is ±9 Nm (static) and ±15 Nm (dynamic). Each motor incorporates an electric brake to ensure that the cables remain in tension when the power is turned off. Each motor has a built-in high resolution encoder capable of measuring joint angle in increments of 0.006°. In addition, secondary encoders may be mounted directly to each of the three joints.

3.3.2 Performance

The exoskeleton was assembled and initial tests confirmed that joint angles were correctly calculated using cable length changes. The robot could be moved passively while pretension was applied to all cables, and torques could be applied independently and across multiple joints. Basic position control was implemented, and end-point force-fields simulating a virtual wall could also be applied. Measurements of the exoskeleton's friction, inertia and compliance as seen by the joints of the limb were measured.

Figure 13A:
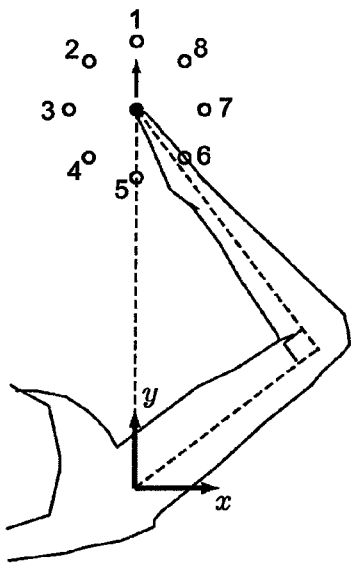
FIGS. 13a to 13c show reaching data obtained with the robotic exoskeleton of FIGS. 10, 11a, 11b, and 12.
Figure 13B:
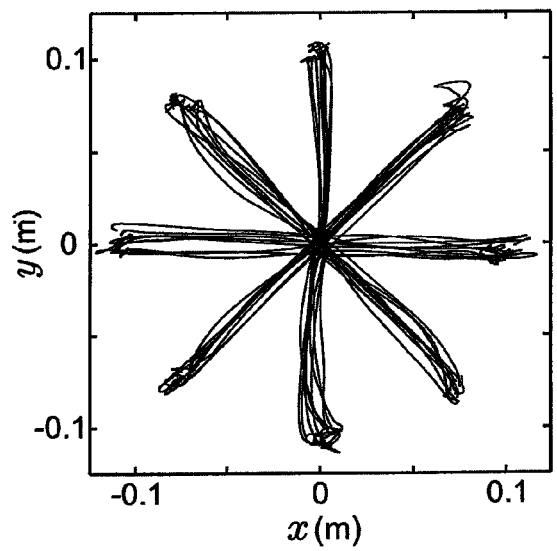
Figure 13C:
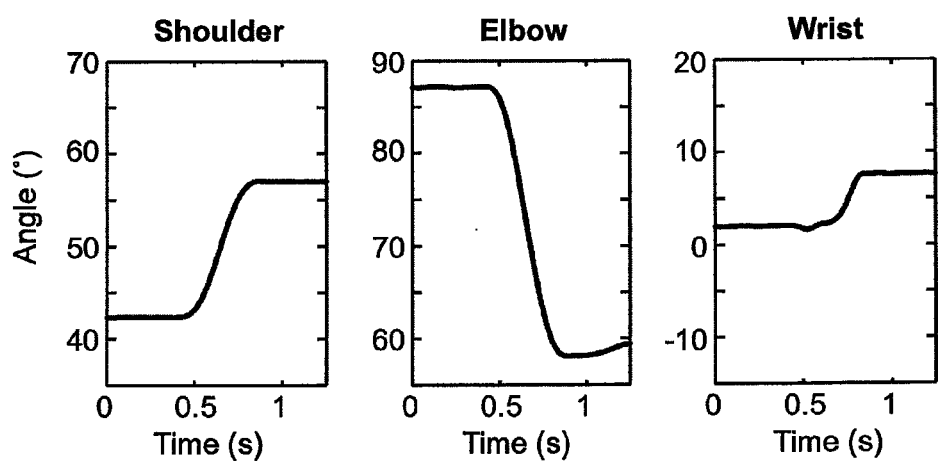

FIGS. 13a to 13c show results from a basic reaching task using the exoskeleton. FIG. 13a shows the task design. The subject performed reaching movements from a central target to eight peripheral targets as shown. The angles of the shoulder, elbow and wrist were recorded by a data acquisition system connected to position sensors on the joints of the exoskeleton during the reaching movements. The hand paths during the outwards reaching movements are shown in FIG. 13b. FIG. 13c shows the individual joint angles for one movement.

4 Three-Dimensional (3-D) Robotic Exoskeleton

A limitation with currently available robotic exoskeletons is that few are capable of replicating the full range of motion of the human shoulder complex. In particular, shoulder girdle motion is poorly replicated. A prior robotic device (see U.S. Patent Publication No. US2003/0115954A1) provides two DOF at the sternoclavicular joint, but in that design some equipment for these two axes is located on the two joint axes, resulting in equipment being located near and around the user's head. The embodiment described below overcomes this limitation.

Accordingly, another embodiment of the invention relates to a robotic exoskeleton that provides six degrees of freedom (DOF), allowing for the substantially full range of articulation of the upper limb to be assessed and/or rehabilitated. When configured for use with the upper limb, the robotic exoskeleton of the current embodiment provides independent control of all five major DOFs at the shoulder complex by coupling five exoskeleton joints to the five axes of rotation that represent the 5DOF of the shoulder complex. In particular, 2 exoskeleton joints are coupled to the sternoclavicular joint with all equipment located behind the user, and no equipment is placed above the user's head. This embodiment represents a substantial improvement over other known robotic devices, which either cannot provide control of all five major DOFs of the shoulder complex or do so in a manner requiring equipment above and near the user's head. Key features of the exoskeleton include:

Independent control of five DOF of the shoulder complex (two DOF at the sternoclavicular joint, three DOF at the glenohumeral joint), and one DOF at the elbow, with a workspace similar to a typical upper limb workspace.

Actuators and exoskeleton sized to accommodate subjects from 1.4 m to 2.0 m in height, and weighing up to 115 kg.

High back-driveability, low mass and inertia to minimize influence on natural motion.

Allows simplification of the mechanism to two DOF shoulder/elbow motion in any plane.

Avoids singular configurations throughout the workspace.

Maximizes manipulability across the workspace.

Safe and comfortable for subjects with motor impairments.

Quick and easy to set up for a subject.

Figure 14:
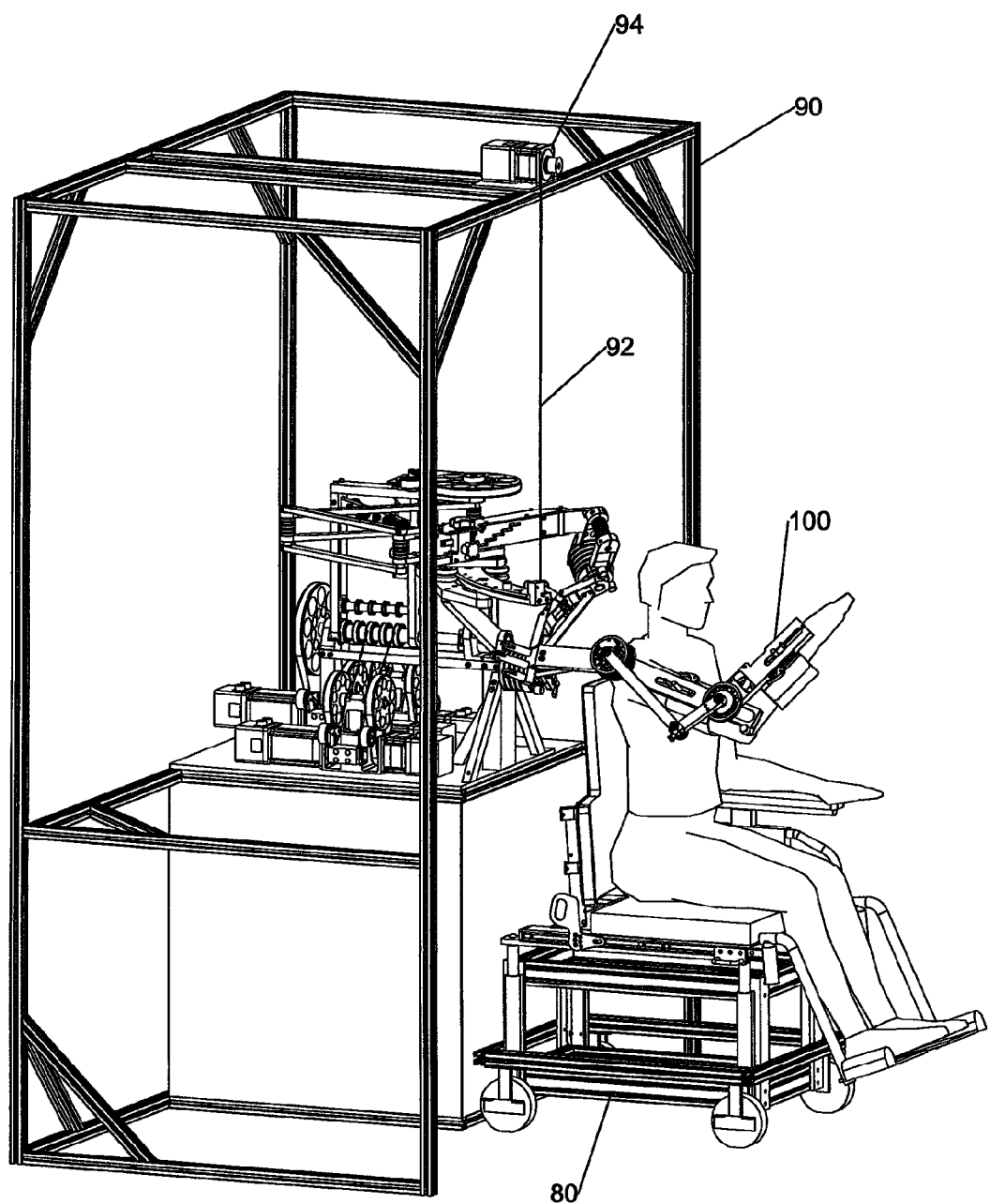
FIG. 14 is a diagram showing a six DOF 3-D robotic exoskeleton according to an embodiment of the invention.

FIG. 14 shows an embodiment of the 3-D robotic exoskeleton configured for the right upper limb. The exoskeleton 100 is mounted to a support structure 90, and the subject is wheeled into position using a movable chair 80. There is space for the operator to get beside the exoskeleton during the set-up procedure. The exoskeleton consists of two main subsystems: the shoulder/elbow mechanism (four DOF to move the upper arm and forearm), and the shoulder girdle mechanism (two DOF to move the glenohumeral joint relative to the torso about the sternoclavicular joint).

The term "sternoclavicular joint axes" as used herein, refers to the two axes of rotation that represent the two DOF of the sternoclavicular joint, and the term "sternoclavicular joint centre" as used herein refers to the point of intersection of the sternoclavicular joint axes. The term "glenohumeral joint axes" as used herein, refers to the three axes of rotation that represent the three DOF of the glenohumeral joint, and the term "glenohumeral joint centre" as used herein refers to the point of intersection of the glenohumeral joint axes.

This six DOF embodiment incorporates embodiments described in previous sections, above. For example:

A) Coupling about the second axis of the sternoclavicular joint (shoulder girdle mechanism) is based on the off-axis remote coupling of the embodiment shown in FIG. 2b.

Figure 17:
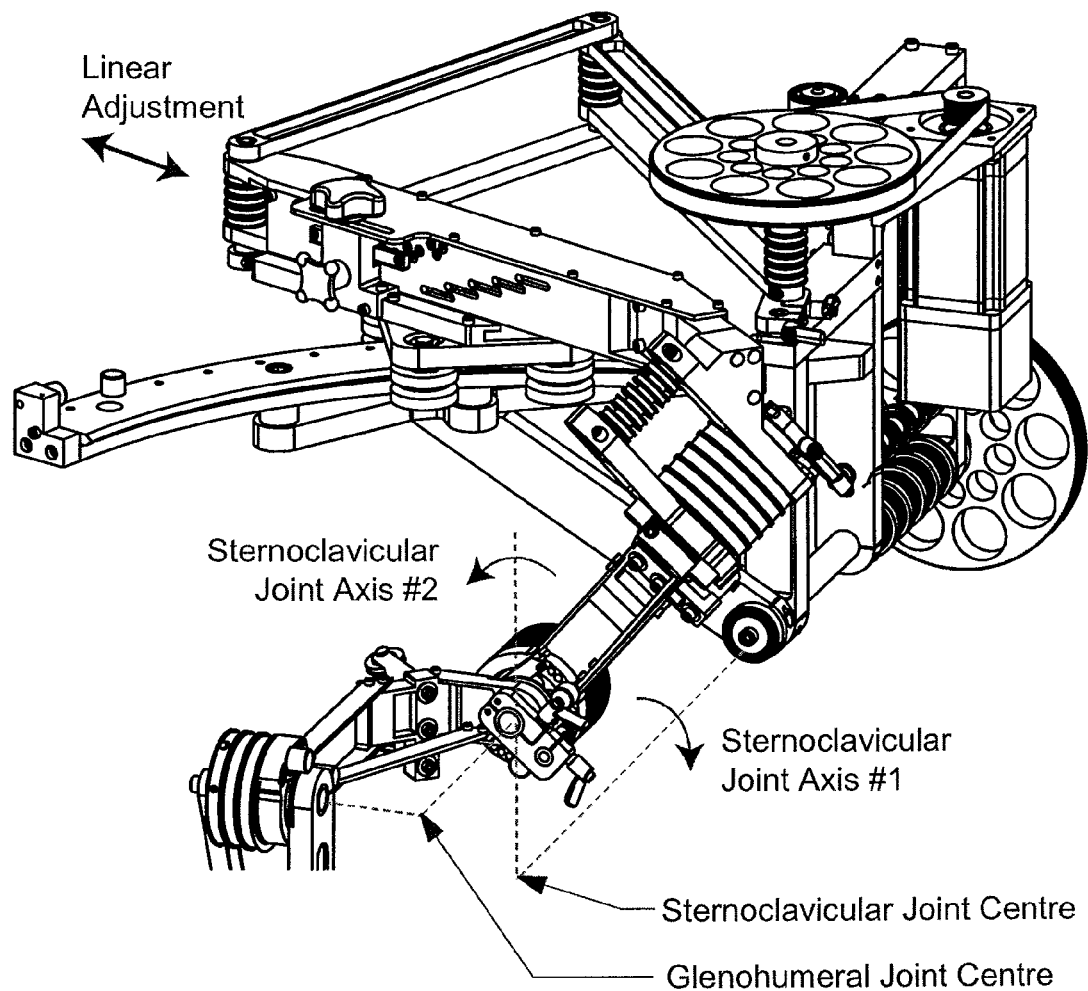
FIG. 17 is a drawing of the shoulder girdle mechanism of the exoskeleton of FIG. 14, which includes the curved track linkage of FIG. 2b.

B) On-axis remote coupling about all three axes at the glenohumeral joint is based on the embodiment of FIG. 6b, in which the second coupled joint (FIG. 17, located near the "linear adjustment" arrow) acts as a driving joint itself, and is coupled to the glenohumeral joint axes through cables and pulleys.

C) The elbow joint axis is on-axis remotely coupled in the same manner as the glenohumeral joint axes and in addition includes a mechanical linkage based on the embodiment of FIG. 6c, between the last glenohumeral joint axis and the elbow joint (i.e., the driving joint of the mechanical linkage is located at the last glenohumeral joint axis, but this joint itself is coupled back to a motor on ground, as described in B, above). This allows the length of the link joining the elbow joint axis and the last glenohumeral joint axis to be adjusted for different upper arm lengths. The 3-D exoskeleton is not limited to the structure described herein, as other configurations and arrangements of mechanical linkage are possible so as to couple more or fewer joints of a limb, and/or provide more or fewer DOFs to one or more selected joints of a limb.

By incorporating the design features described above, the three-dimensional (3-D) exoskeleton provides beneficial features including, but not limited to, location of motors and mechanical linkage away from the subject's head. As with the planar exoskeleton described above, the 3-D exoskeleton may be used for assessing and diagnosing motor function deficits in subjects, as well as for rehabilitation, therapy, and research.

4.1 Shoulder/Elbow Mechanism

The shoulder/elbow mechanism (FIG. 15a) is a four DOF mechanism in which the three axes of a three DOF spherical joint are coupled to the three joint axes of the glenohumeral joint and a single rotary joint is coupled to the elbow joint. It is actuated entirely by a cable-drive transmission which is driven by five electric motors located on the base (ground) of the exoskeleton. The overall gear ratio (i.e., the gear reduction happens in two stages:one occurs where the cables are wound up, and the second occurs at the motor using timing belts) for each of the four joints is set such that the robot maintains back-driveability without the need for force/torque sensors. An overall gear ratio of eight has been found to be suitable. The lightweight mechanism is attached to the lateral side of the subject's arm using two adjustable arm cuffs, which are the only points of physical attachment to the subject. Inflatable or padded arm cuffs may be used for greater comfort.

4.1.1 Orientation of the Three Glenohumeral Joint Axes

Glenohumeral motion is achieved using a spherical joint made from three intersecting revolute joint axes connected in series. A major problem with spherical joints is that it is always possible to reach a singular configuration (where one DOF is lost) by rotating the second joint axis so that the three axes become coplanar. The order and relative orientation of these three axes was optimized to ensure that the exoskeleton does not reach singularity within the subject's workspace (as specified in Ball et al., 2007a), that manipulability is maximized, and that collision with the subject or itself does not occur over the entire workspace. The optimization process is described below.

It will be appreciated that it is useful to be able to mechanically lock the six DOF mechanical linkage into a planar two DOF exoskeleton (one DOF shoulder and one DOF elbow motion only) in any plane (i.e., not limited to vertical or horizontal). This would allow the mechanical linkage to function in a simpler configuration, which may be more appropriate for some assessment or treatment purposes. To achieve this, the third joint axis of the spherical joint (the last glenohumeral joint axis) is chosen to be parallel to the elbow joint axis (see FIG. 15a). Thus, the first four joint axes of the mechanical linkage (both joint axes of the sternoclavicular joint and the first two axes of the glenohumaral joint) can be positioned to select the desired plane, and then physically locked. When locked, the first four joint axes of the mechanical linkage are not part of the simplified planar linkage's motion.

With the third glenohumeral joint axis orientation chosen, the orientations of the remaining two joint axes were then determined as follows. It was straightforward to determine that the second joint axis should be perpendicular to the third axis (and in the horizontal plane) in order to avoid singularities in the workspace. This configuration also has the added benefit of allowing basic flexion/extension or adduction/abduction motions to be controlled using a single joint axis.

Figure 15A:
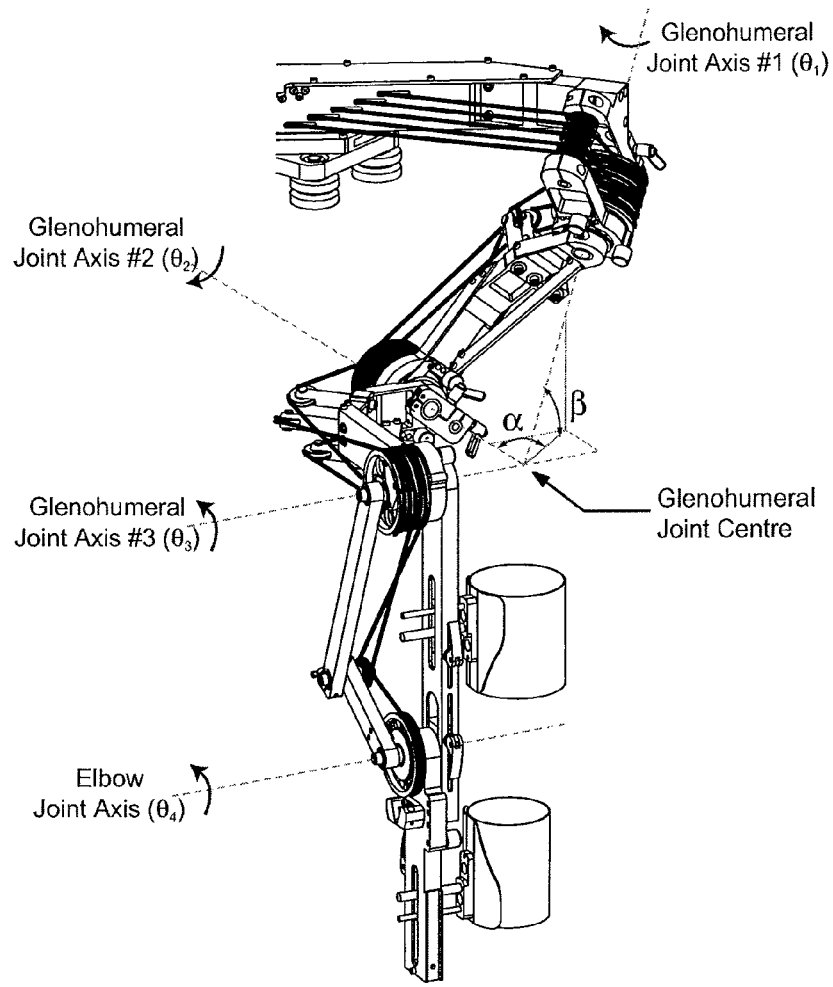
FIG. 15a is a drawing of the shoulder/elbow mechanism of the exoskeleton of FIG. 14, showing the joint orientations and the cable drive system.

To determine the optimal first joint axis orientation, an iterative procedure was developed to calculate the box product, M, at each configuration in the workspace. The box product is defined as:

$$M = z_1 \times (z_2 \times z_3) \quad (3)$$

where $z_i$ are the unit vectors corresponding to the glenohumeral joint axes. When M=1, the joint axes are orthogonal and manipulability is maximized. When M=0, the joint axes are coplanar and a degree of freedom is lost (i.e., singular configuration). The procedure is summarized as follows, and step-by-step results are shown in FIGS. 16a to 16d:

1) The orientation of the first joint axis was defined relative to the second joint axis in terms of two optimizable parameters ($\alpha$ and $\beta$, as shown in FIG. 15a).

Figure 16A:
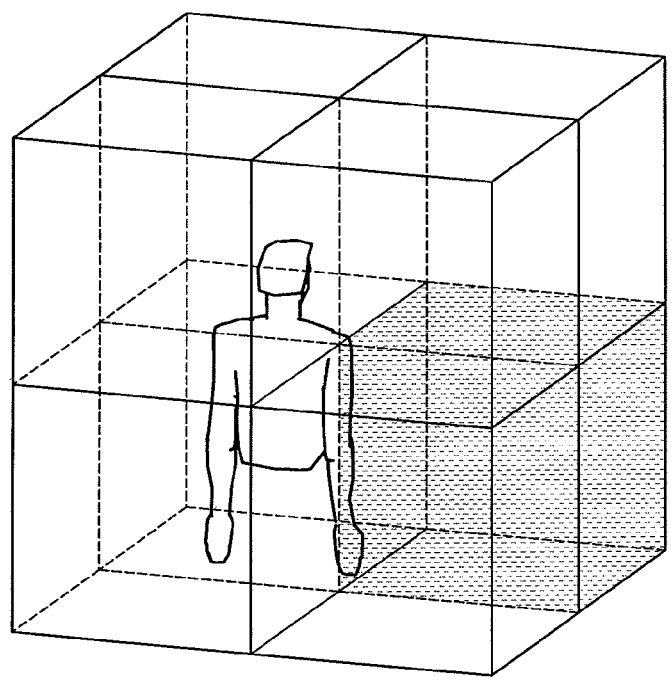
FIG. 16a shows the coordinate frame used for the joint orientation optimization calculations for the embodiment of FIG. 14. The shaded octant approximates the humeral workspace.
Figure 16B:
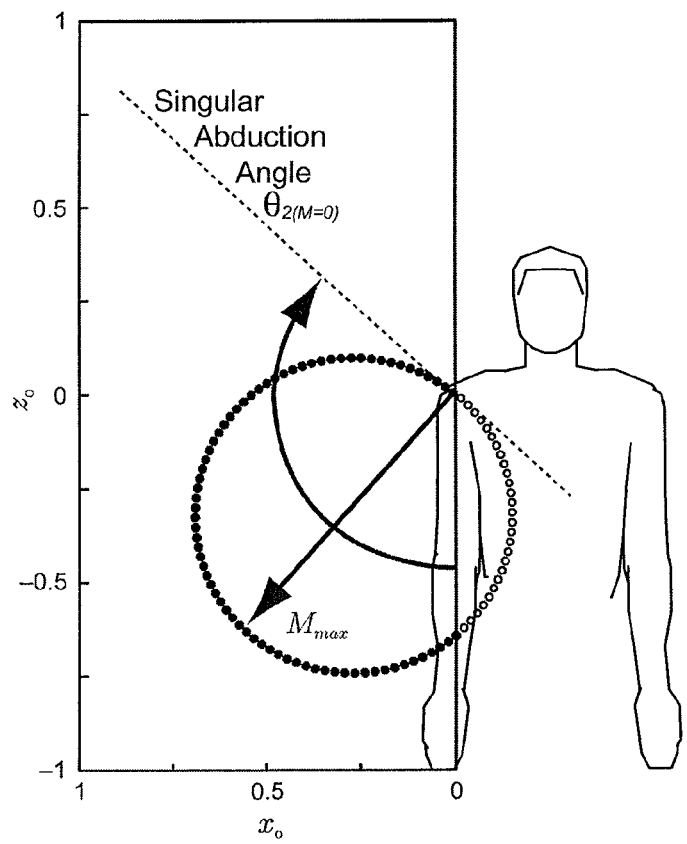
FIG. 16b is a plot of manipulability (M) for a given combination of optimization parameters α, and β, as $\theta_2$ is varied to obtain the singular abduction angle ($\theta_{2(M=0)}$) and the maximum manipulability ($M_{max}$).

2) With $\theta_1$ and $\theta_3$ fixed, manipulability (M) was calculated for a combination of $\alpha$ and $\beta$ as $\theta_2$ was varied (corresponds to abduction, as shown in FIG. 16b).

Figure 16C:
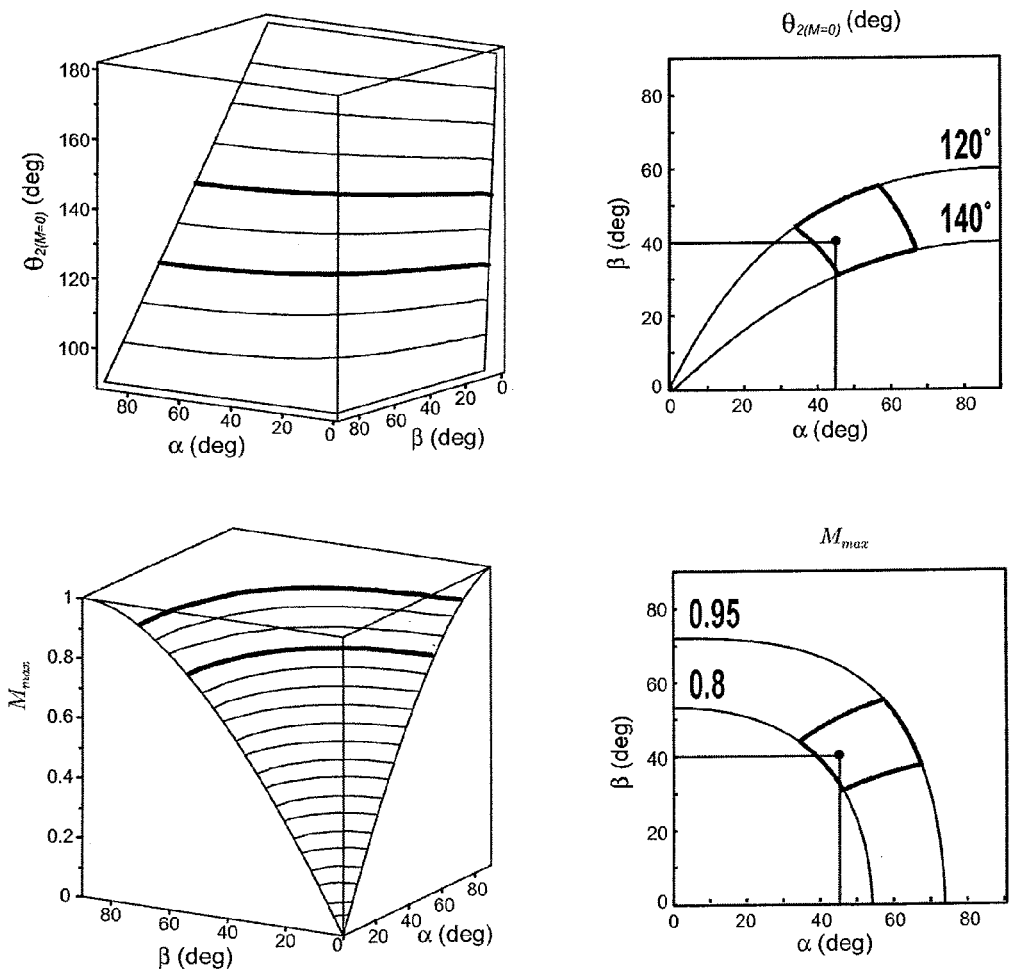
FIG. 16c is a plot of $\theta_{2(M=0)}$ and $M_{max}$ for all combinations of α and β. The range of α and β combinations that provides a suitable compromise between $\theta_{2(M=0)}$ and $M_{max}$ is shown by contour lines, and the overlap is highlighted.

3) The singular abduction angle ($\theta_{2(M=0)}$) and the maximum manipulability ($M_{max}$) were calculated and plotted for all combinations of $\alpha$ and $\beta$ (FIG. 16c).

4) A range of $\alpha$ and $\beta$ combinations that reached a feasible compromise between high $M_{max}$ and large $\theta_{2(M=0)}$ was revealed (i.e., $0.8 < M_{max} < 0.95$ and $120° < \theta_{2(M=0)} < 140°$). The following iterative procedure was then used to select a combination of $\alpha$ and $\beta$ within this range.

Figure 16D:
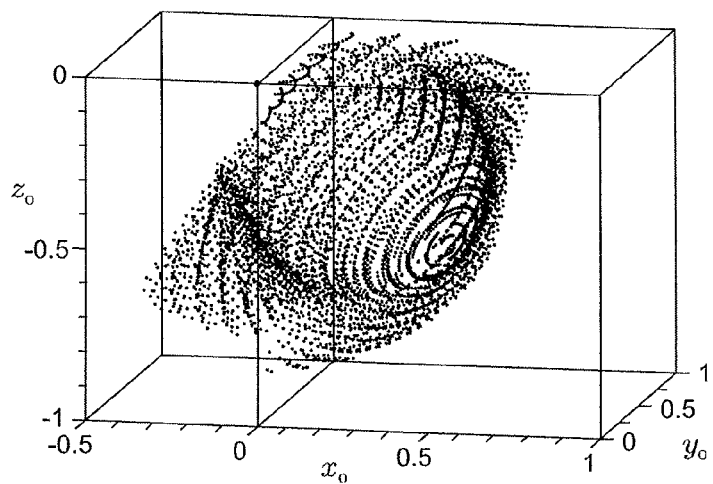
FIG. 16d shows $M_{max}$ plotted radially over the workspace. Points closer to the origin are configurations that are closer to singularity.

5) M was calculated for the entire workspace of the spherical joint for a given $\alpha$ and $\beta$ (all three joints varied across their ranges of motion, as shown in FIG. 16d).

6) If any points were within 10° of singularity (M<0.15) or if the exoskeleton could collide with the subject, the process was repeated from step 5 using a different combination of $\alpha$ and $\beta$.

7) The process was repeated until there were no singularities in the workspace, and the manipulability was as high as possible over the workspace.

The final angles that provided the optimal spherical joint axes arrangement for the given design constraints are $\alpha=45°$ and $\beta=40°$. The maximum manipulability is 0.85 and averages 0.75 across the workspace.

4.1.2 Cable-Drive System

The joint axes of the shoulder/elbow mechanism are on-axis remotely coupled through the shoulder girdle mechanism (which is described in Section 4.2 below) with an open-ended cable drive transmission actuated by electric motors. Cable-driven mechanisms have a high power-to-weight ratio because all the motors can be placed on the fixed base (i.e., ground). This significantly reduces the size, mass and inertial properties of the robot, and helps to reduce the motor torque output requirements. Open-ended cable systems distribute loads across several cables, which also reduces the actuator requirements. Overall the mechanism becomes more transparent (i.e. less perceptible) to the subject.

Open-ended cable-drive systems require additional transformations to control the robot (Tsai, 1999). This is due in part to the fact that the number of joints needing control (n) is less than the number of actuators (m). Cable systems can apply force through tension only, so it is necessary to have an antagonistic cable routing scheme for motion capability in both rotational directions at each joint. As such, a minimum of n+1 cables are necessary for complete control of n joints. Also, it is necessary to have a positive tension in all cables at all times to prevent the cables from becoming slack. Furthermore, since the cables are routed along the entire length of the mechanism through a series of pulleys, their motion affects multiple joints, allowing loads at the joints to be distributed among the actuators. Ultimately, joint angles and torques are related to the length displacement and the forces in the cables.

Figure 15B:
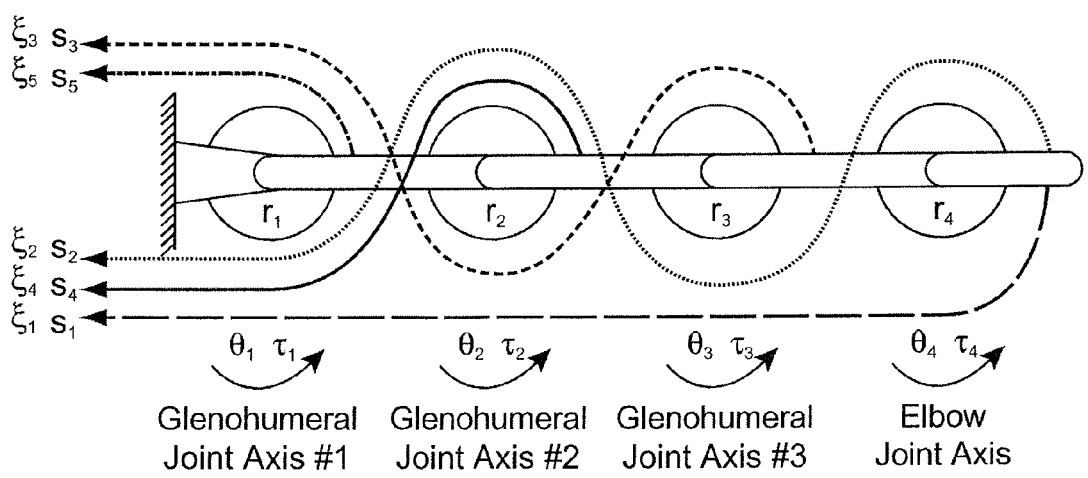
FIG. 15b is a simplified planar schematic representation of the optimal cable routing scheme of the embodiment of FIG. 15a. Each joint of the exoskeleton has a separate pulley for each cable that passes by the joint. Symbols s, ξ, r, τ, and θ represent cable displacement, cable force, pulley radius, joint torque, and joint angle, respectively.

The choice of cable routing scheme has a significant effect on the performance of the device. In fact, for this four DOF mechanical linkage (n=4) actuated by five motors (m=5), there are 11 possible unique cable routing schemes, all of which can be described in matrix form. This matrix can be analyzed to obtain quantitative measures related to efficiency and actuator torque requirements (Lee, 1991). FIG. 15b illustrates the optimal routing scheme which has minimal antagonism between cables and hence the most even distribution of forces across the cables, and also has the lowest peak forces.

4.1.3 Joint Design

Each joint of the exoskeleton requires a low friction bearing system that provides rotation about its axis while providing rigidity against forces and moments in all other directions. In addition to withstanding non-axial gravitational and inertial moments during motion, the joints must withstand substantial non-axial moments resulting from forces applied by the cables and pulleys. Four-point contact bearings are highly resistant to non-axial moments and therefore need not be used in pairs. Use of four-point contact bearings results in a thin and lightweight exoskeleton.

4.2 Shoulder Girdle Mechanism

The shoulder girdle mechanism (FIG. 17) provides two DOF about the subject's sternoclavicular joint: elevation/depression and protraction/retraction. The entire mechanism is located behind the subject, and there is an adjustment to account for subjects of different size. The mechanism supports the complete shoulder/elbow linkage including the subject's arm, and as a result must be structurally strong.

The first sternoclavicular joint of the exoskeleton is fixed to ground at the base structure behind the subject, with its axis pointing forward in the horizontal plane. It is a conventional rotary joint that provides elevation/depression motion. The second joint axis is vertically aligned, and intersects the first joint axis through the subject's sternoclavicular joint, allowing protraction/retraction motion. This second joint axis provides off-axis remote coupling to the subjects's sternoclavicular joint, based on the embodiment in FIG. 2b. It is not a typical rotary joint; rather, it is a curved track linkage on which a carriage travels (as described above with respect to the planar exoskeleton). The low-friction carriage supports the entire cable drive system and is driven by a hinged linkage. The cables that drive the shoulder/elbow mechanism are coupled through this hinged linkage, similar to the embodiment in FIG. 6b. The resulting mechanism operates like a four-bar mechanical linkage without requiring any structural elements near the subject's sternoclavicular joint (see FIG. 17). Both joints are driven by electric motors with timing belts, and operate with gear ratios of for example, 5 and 6.25, respectively.

The benefits of the track linkage are significant. First, it facilitates placing equipment behind the subject rather than above the subject's head, which is safer and more comfortable for the subject, and also easier for the operator to set up. Second, the hinged driving linkage doubles as a routing system for the cables from the shoulder/elbow mechanism by guiding them through to the base of the robot without any non-linear changes in cable length. Any change in cable length as a result of shoulder girdle motion is easily accounted for in the cable length transformations.

The weight of this mechanism is substantial, and puts high static torque requirements on the first shoulder girdle joint. To remove part of the burden from the motor, an external gravity compensation system may be employed. For example, a vertical cable 92 may be connected to the curved track and controlled by a third motor 94 mounted to the frame 90 directly above the end of the track (see FIG. 14), to apply a vertical force on the track to offset the gravitational forces on the exoskeleton.

4.4 Subject Attachment and Alignment

To function correctly, the joints of the exoskeleton must be aligned with the sternoclavicular and glenohumeral joints of the subject, and adjusted to fit arms of different lengths. A harness attached to the moveable chair 80, is secured around the subject's torso, and the chair may be used to obtain the three translational adjustments necessary to align the subject's sternoclavicular joint with the exoskeleton's fixed sternoclavicular joint centre. Once aligned, the chair is locked to the main structure 90.

The exoskeleton must next be aligned with the subject's glenohumeral joint centre. As before, three spatial adjustments are required. However, this can be achieved by a single manual linear adjustment because the redundancy of the exoskeleton structure can be used to make the remaining alignments. This linear adjustment shifts the cable-drive system relative to the carriage in the direction approximately aligned with the horizontal projection of the clavicle (see FIG. 17) and is then clamped to the carriage. This design is based on the embodiment shown in FIG. 6b. Thus modifying the position of the exoskeleton's glenohumeral joint centre is achieved through the linear adjustment and the two DOF provided by the shoulder girdle mechanism. The three DOF spherical joint of the shoulder/elbow mechanism automatically compensates by rotating until the exoskeleton is properly aligned with the subject's limb.

This adjustment scheme has the benefit of simplifying the structure of the exoskeleton's sternoclavicular joint, and also the set-up procedure. Otherwise, three consecutive translational adjustments would be required, making the robotic exoskeleton significantly larger, heavier and more complicated. Relying on the shoulder/elbow mechanism to compensate for the adjustment tends to push the robot shoulder joint away from its optimal configuration, decreasing the range of motion of the exoskeleton in some directions. However, the adjustment range is typically small (2° or 3° at most), so the singularities and manipulability of the exoskeleton will not be significantly altered. Another issue that arises when adjusting an open-ended cable-drive system is that it is necessary to maintain tension in the cables at all times. Adjusting the link length must not change the cable length, otherwise tension would be lost. Use of a hinged linkage based on the embodiment of FIG. 6b ensures that the cable length does not change and that tension is maintained.

Figure 18A:
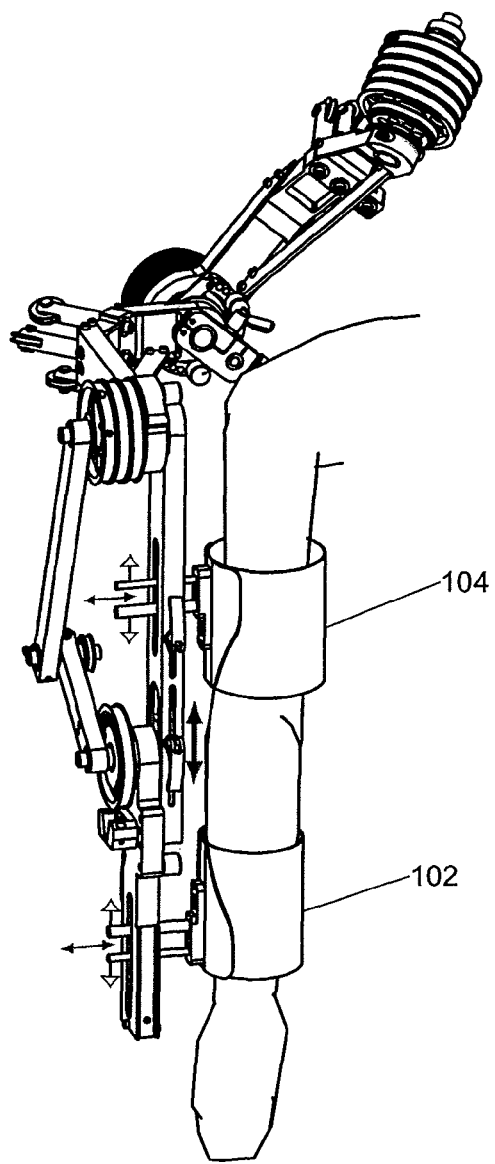
FIG. 18a is a drawing of the arm cuff attachments and adjustments of the exoskeleton of FIG. 14. Each cuff has two translational adjustments to correctly align the limb segments relative to the mechanism structure: perpendicular to the link (small arrows) and parallel to the link (hollow arrows). A fifth adjustment (large arrow) moves the location of the elbow joint to change the length of the upper limb link.

The exoskeleton attaches to the subject in two places: the upper arm and the forearm (FIG. 18a). These attachments keep the exoskeleton aligned with the limb at all times. For example. attachment of the limb may be accomplished by strapping the limb into rigid half-cylindrical troughs using a inflatable Velcro™ straps or cuffs 102, 104 similar to a blood pressure cuff. Once strapped in, the cuffs may then be inflated to provide a secure fit that is customized to the subject. The cuffs may be attached to the subject before connecting to the exoskeleton, which is easier for the operator, and more comfortable for the subject. An important difference from many previous aim cuff designs is that the arm cuff does not have a fixed size through which the subject must put their arm. This allows simpler set up, and also is compatible with a larger variety of arm sizes.

Figure 18B:
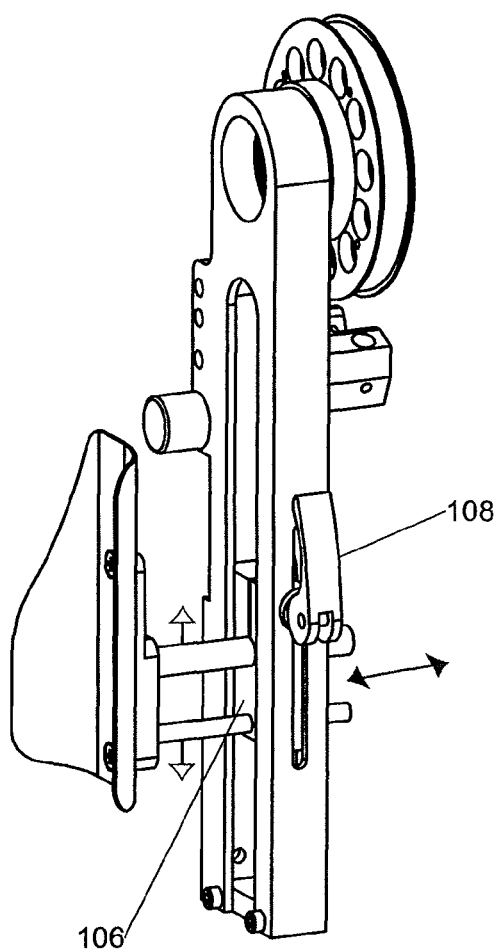
FIG. 18b is a close-up of the cuff attachment, showing a quick-release clamp.

Five adjustments are required to ensure that the subject's arm is properly aligned with the exoskeleton (see FIG. 18a). Each cuff is adjustable along the length of the exoskeleton (for limbs of different length) and perpendicular to the exoskeleton (for limbs of different width). For example, as shown in FIGS. 18a and b, each cuff may have two translational adjustments to correctly align the limb segments relative to the mechanism structure: perpendicular to the link (small arrows) and parallel to the link (hollow arrows). A fifth adjustment (large arrow) moves the location of the elbow joint to change the length of the upper limb link. For example, the cuff may be attached by inserting it into a slider 106 which can move freely along the exoskeleton. A quick-release clamp 108 (e.g., a cam-operated clamp) may be used to simultaneously clamp the cuff to the slider and the slider to the exoskeleton (see FIG. 18b). To accommodate subjects with different arm lengths, a similar slider and clamp may be used to locate the elbow joint along the upper arm link. Using a mechanical linkage based on the embodiment of FIG. 6c to couple the last shoulder joint to the elbow joint ensures that the joints remain coupled and that cable tension is not lost when adjusting the upper arm length.

Although exoskeleton-type robotic devices always require more set up time than their end-effector-type counterparts, the exoskeleton described herein has a relatively simple set up procedure and yet provides substantial mobility and adjustability. In fact, once the wheeled chair is locked in place, only four clamps are required to secure all eight adjustments. This minimizes set up time, leaving more time for therapy.

4.5 Dynamic Model and Simulation

To help make appropriate choices for the eight electric motors required to actuate the 3-D exoskeleton, a dynamic model of the exoskeleton and the human limb was created in MATLAB based on the robot toolbox (Corke, 1996). The model was also used to specify a number of other design parameters including bearing strength, joint gear ratios, and cable load capacity.

The exoskeleton was modeled as a standard rigid-body manipulator, and it was assumed that the cable dynamics were not significant. Dynamic parameters of the exoskeleton, including lengths, masses, and inertial properties were estimates from CAD drawings. The same properties of the human upper limb were calculated from anthropometric data tables based on subject height and weight (Winter, 1990) and were fully integrated into the model. The model was adapted to account for the external gravity compensation system, and included estimates of viscous and static friction. Given a trajectory for each joint, the model calculated the joint torques required to achieve that motion. The cable forces required to generate the joint torques were then calculated using the torque resolver technique (Lee, 1991). The final output was the torque outputs for all eight motors, the force in each cable, and all forces and non-axial moments at each joint.

To get an estimate of the peak dynamic motor torques for non-contact applications, the model was used to simulate various reaching movements with a peak end-point velocity of 1.0 m/s. Anthropometric limb measurements were chosen to meet the maximum design requirements. Movements included single joint movements through the full range of motion of each joint, and a range of typical multi-joint reaching movements such as reaching towards the face or chest from a relaxed position. The most demanding positions for the exoskeleton in terms of static torque requirements are those in which the arm is raised to the horizontal plane with the elbow fully extended. The gravitational component of the joint torques is the most significant contribution, and produces the largest stresses on the motors in static situations, so each position was held for one second to facilitate measurements of peak static torque.

Motors and gear ratios were selected based on the results of these simulations. The motors have built-in high resolution encoders capable of measuring joint angle in increments of 0.003°. Each motor also incorporates an electric brake to guarantee that the mechanism will not collapse during a power failure. The brakes also ensure that the cables remain in tension when the power is turned off. The simulations also enabled selection of a braided stainless steel cable of appropriate size, and also joint bearings with sufficient load capabilities. The overall torque capabilities of each joint of the exoskeleton are shown in Table I, and are a result of the limits of both the motors and the cable strength.

TABLE 1

| Maximum Torque Output for Each Joint | | |
| --- | --- | --- |
| Motor | Static Torque (Nm) | Peak Torque (Nm) |
| Shoulder Girdle #1 | ±24 | ±73 |
| Shoulder Girdle #2 | ±30 | ±91 |
| Glenohumeral #1 | +39, −26 | ±60 |
| Glenohumeral #2 | +39, −26 | ±60 |
| Glenohumeral #3 | +39, −26 | ±60 |
| Elbow | ±13 | +40, −30 |

All cited publications and patent documents are incorporated herein by reference in their entirety.

Equivalents

Those skilled in the art will recognize or be able to ascertain variants of the embodiments described herein. Such variants are within the scope of the invention and are covered by the appended claims.

REFERENCES

Ball, S. J., Brown, I. E., and Scott, S. H., "A planar 3DOF robotic exoskeleton for rehabiliation and assessment," in 29th Annual Internation Conference of the IEEE Engineering in Medicine and Biology Society (EMBC'07), pp. 4024-4027, Lyon, France, Aug. 22-26, 2007c.

Ball, S. J., Brown, I. E., and Scott, S. H., "Designing a robotic exoskeleton for shoulder complex rehabilitation," in 30th Canadian Medical and Biological Engineering Conference (CMBEC30), Toronto, Canada, Jun. 16-19, 2007b.

Ball, S. J., Brown, I. E., and Scott, S. H., "MEDARM: a rehabilitation robot with 5DOF at the shoulder complex," in Proc. IEEE/ASME International Conference on Advanced Intelligent Mechatronics (AIM'07), Zurich, Switzerland, Sep. 4-7, 2007a.

Burgar, C. G., Lum, P. S., Shor, P. C., and Machiel Van der Loos, H. F., "Development of robots for rehabilitation therapy: the Palo Alto VA/Stanford experience," J. Rehabil. Res. Dev., vol. 37, no. 6, pp. 663-673, 2000.

Corke, P. I., "A robotics toolbox for MATLAB," IEEE Robot. Automat. Mag., vol. 3, no. 1, pp. 24-32, 1996.

Dobkin, B. H., "Strategies for stroke rehabilitation," Lancet Neurol., vol. 3, no. 9, pp. 528-536, 2004.

Frisoli, A., Rocchi, F., Marcheschi, S., Dettori, A., Salsedo, F., and Bergamasco, M. "A new force-feedback arm exoskeleton for haptic interaction in virtual environments". In Proc. 1st Joint Eurohaptics Conference and Symposium on Haptic Interfaces for Virtual Environments and Teleoperator Systems, pp. 195-201, 2005.

Hesse, S., Schmidt, H., Werner, C., and Bardeleben, A., "Upper and lower extremity robotic devices for rehabilitation and for studying motor control," Curr. Opin. Neurol., vol. 16, no. 6, pp. 705-710, 2003.

Johnson, G. R., Carus, D. A., Parrini, G., Scattareggia, M. S., and Valeggi, R., "The design of a five-degree-of-freedom powered orthosis for the upper limb," Proc. Inst. Mech. Eng [H.], vol. 215, no. 3, pp. 275-284, 2001.

Krebs, H. I., Hogan, N., Aisen, M. L., and Volpe, B. T., "Robot-aided neurorehabilitation," IEEE Trans. Rehabil. Eng, vol. 6, no. 1, pp. 75-87, 1998.

Lee, J. J., "Tendon-driven manipulators: Analysis, synthesis, and control," Ph.D. Thesis, University of Maryland, 1991.

Loureiro, R., Amirabdollahian, F., Topping, M., Driessen, B., and Harwin, W., "Upper limb robot mediated stroke therapy—GENTLE/s approach," Autonomous Robots, vol. 15, no. 1, pp. 35-51, 2003.

Mihelj, M., Nef, T., and Riener, R., "ARMin—toward a six DoF upper limb rehabilitation robot," Proceedings of the First IEEE/RAS-EMBS International Conference on Biomedical Robots and Biomechatronics, pp. 1154-1159, 2006.

Mihelj, M., Nef, T., and Riener, R., "ARMin II—7 DoF rehabilitation robot: mechanics and kinematics". In Proc. IEEE International Conference on Robotics and Automation (ICRA'07), pp. 4120-4125, 2007.

Nef, T., and Riener, R. "ARMin—Design of a novel arm rehabilitation robot". In Proc. IEEE 9th International Conference on Rehabilitation Robotics (ICORR'05), pp. 57-60, 2005.

Perry, J. C., and Rosen, J. "Design of a 7 Degree-of-Freedom Upper-Limb Powered Exoskeleton". In Proc. IEEE/RAS-EMBS International Conference on Biomedical Robots and Biomechatronics (BIOROB'06), 2006

Reinkensmeyer, D. J., Emken, J. L., and Cramer, S. C., "Robotics, motor learning, and neurologic recovery," Annu. Rev. Biomed. Eng, vol. 6, pp. 497-525, 2004.

Sanchez, R. J., Reinkensmeyer, D., Shah, P., Liu, J., Rao, S., Smith, R., Cramer, S., Rahman, T., and Bobrow, J., "Monitoring functional arm movement for home-based therapy after stroke," in Proc. IEEE Annual Conference of Engineering in Medicine and Biology Society (EMBC'04), vol. 2, 2004, pp. 4787-4790.

Sanchez, R. J., Liu, J., Rao, S., Shah, P., Smith, R., Rahman, T., Cramer, S. C., Bobrow, J. E., and Reinkensmeyer, D. J. "Automating arm movement training following severe stroke: Functional exercises with quantitative feedback in a gravity-reduced environment," IEEE Transactions on Neural Systems and Rehabilitation Engineering, vol. 14, no. 3, pp. 378-389, 2006.

Scott, S. H., "Apparatus for measuring and perturbing shoulder and elbow joint positions and torques during reaching," J. Neurosci. Methods, vol. 89, no. 2, pp. 119-127, 1999.

Teasell, R., Foley, N., Jutai, J., Doherty, T., Bitensky, J., Bhogal, S., and Speechley, M., "Stroke rehabiliation evidence-based review: Upper extremity interventions," Monograph on the Internet, 2003.

Tsai, L.-W., Robot Analysis: The Mechanics of Serial and Parallel Manipulators. New York: John Wiley & Sons, Inc., 1999.

Winter, D. A., Biomechanics and Motor Control of Human Movement, 2nd ed. New York, U.S.A: John Wiley & Sons, Inc., 1990.

Zatsiorsky, V. M., Kinematics of Human Motion, Champaign, Ill., U.S.A: Human Kinetics, 1998.

The invention claimed is:

1. A method for assessing, studying, or assessing and studying sensorimotor function of a limb of a subject, comprising:
coupling a virtual joint of a first robotic mechanical linkage to a first selected joint of the limb of the subject;
wherein an axis of the virtual joint is not located on the first robotic mechanical linkage;
wherein the first robotic mechanical linkage is not located on or along an axis of the coupled first selected joint of the limb;
wherein the first robotic mechanical linkage includes a second joint that is not located on an axis of the first selected joint of the limb when the limb is coupled to the linkage; and
wherein the first robotic mechanical linkage includes at least two links that couple the virtual joint to the second joint of the robotic mechanical linkage;
wherein coupling provides that motion or torque about an axis at one or more selected joint of the limb will produce a related motion or torque about an axis of one or more selected joint or link of the robotic mechanical linkage;
the method further comprising:
engaging the limb of the subject in a task involving articulation of at least the first selected joint of the limb;
using one or more sensor with the robotic mechanical linkage, wherein the one or more sensor provides one or more signal corresponding to at least one of angular position, torque, and acceleration of the at least one joint or link of the robotic mechanical linkage;
processing the one or more signal to generate data, the data corresponding to at least one of angular position, torque, and acceleration of one or more joints of the limb during the task; and
using the data to assess, study, or assess and study sensorimotor function of the limb of the subject.

2. The method of claim 1, further comprising:
coupling a second robotic mechanical linkage to a second selected joint of the limb, the second robotic mechanical linkage including links for coupling the second robotic mechanical linkage to the second selected joint, with at least one joint having articulation about an axis;
wherein a joint of the second robotic mechanical linkage is located on or along an axis of the second selected joint of the limb.

3. The method of claim 2, further comprising:
coupling a third robotic mechanical linkage to a third selected joint of the limb, the third robotic mechanical linkage including links for coupling the third robotic mechanical linkage to the third selected joint, with at least one joint having articulation about an axis;
wherein a joint of the third robotic mechanical linkage is located on or along an axis of the third selected joint of the limb.

4. The method of claim 1, further comprising:
coupling a second robotic mechanical linkage to the first selected joint of the limb, the first and second robotic mechanical linkages providing two degrees of freedom to the first selected joint; or
coupling a second robotic mechanical linkage and a third robotic mechanical linkage to the first selected joint of the limb, the first, second, and third robotic mechanical linkages providing three degrees of freedom to the first selected joint;
wherein the second robotic mechanical linkage includes links for coupling the second robotic mechanical linkage to the first selected joint and having articulation about an axis that corresponds to a second axis of rotation of the first selected joint of the limb; and
wherein the third robotic mechanical linkage includes links for coupling the third robotic mechanical linkage to the first selected joint and having articulation about an axis that corresponds to a third axis of rotation of the first selected joint of the limb.

5. The method of claim 4, further comprising one of:
(i) coupling a third robotic mechanical linkage to a second selected joint of the limb of the subject;
(ii) coupling a third robotic mechanical linkage to a second selected joint of the limb of the subject and coupling a fourth robotic mechanical linkage to the second selected joint of the limb of the subject, the third and fourth robotic mechanical linkages providing two degrees of freedom to the second selected joint; and (iii) coupling a third robotic mechanical linkage to a second selected joint of the limb of the subject, coupling a fourth robotic mechanical linkage to the second selected joint of the limb of the subject, and coupling a fifth robotic mechanical linkage to the second selected joint of the limb of the subject, the third, fourth, and fifth robotic mechanical linkages providing three degrees of freedom to the second selected joint;

wherein the second robotic mechanical linkage includes links for coupling the second robotic mechanical linkage to the first selected joint and having articulation about an axis that corresponds to a second axis of rotation of the first selected joint of the limb;

wherein the third robotic mechanical linkage includes links for coupling the third robotic mechanical linkage to the second selected joint and having articulation about an axis that corresponds to a first axis of rotation of the second selected joint of the limb;

wherein the fourth robotic mechanical linkage includes links for coupling the fourth robotic mechanical linkage to the second selected joint and having articulation about an axis that corresponds to a second axis of rotation of the second selected joint of the limb; and wherein the fifth robotic mechanical linkage includes links for coupling the fifth robotic mechanical linkage to the second selected joint and having articulation about an axis that corresponds to a third axis of rotation of the second selected joint of the limb.

6. A method for assessing, studying, or assessing and studying sensorimotor function of a limb of a subject, comprising:

coupling a first robotic mechanical linkage to a first selected joint of a limb of a subject, the first robotic mechanical linkage including at least two links for coupling the first robotic mechanical linkage to the first selected joint and having articulation about a first axis that corresponds to an axis of rotation of the first selected joint of the limb;

engaging the limb of the subject in a task involving articulation of at least the first selected joint of the limb;

using one or more sensor with the robotic mechanical linkage, wherein the one or more sensor provides one or more signal corresponding to at least one of angular position, torque, and acceleration of the at least one joint or link of the robotic mechanical linkage;

processing the one or more signal to generate data, the data corresponding to at least one of angular position, torque, and acceleration of one or more joints of the limb during the task; and using the data to assess, study, or assess and study sensorimotor function;

wherein the first axis of rotation of the first robotic mechanical linkage is substantially collinear with the axis of rotation of the first selected joint of the limb;

wherein a second axis of rotation of the first robotic mechanical linkage is substantially collinear with an axis of rotation of a second selected joint of the limb, the second selected joint of the limb being the next joint which is distal or proximal to the first selected joint of the limb; and wherein a distance between the first and second axes of rotation of the first robotic mechanical linkage is variable and coupling of the first and second axes of rotation is maintained without adjusting length of links of the first robotic mechanical linkage.

7. The method of claim 1, comprising assessing, studying, or assessing and studying sensorimotor function of a limb of a healthy subject.

8. The method of claim 1, comprising assessing, studying, or assessing and studying sensorimotor function of a limb of subject with a deficit or an impairment in sensorimotor function.

9. The method of claim 1, further comprising diagnosing, treating, or diagnosing and treating a deficit or an impairment in sensorimotor function of the limb of the subject.

10. The method of claim 6, comprising assessing, studying, or assessing and studying sensorimotor function of a limb of a healthy subject.

11. The method of claim 6, comprising assessing, studying, or assessing and studying sensorimotor function of a limb of subject with a deficit or an impairment in sensorimotor function.

12. The method of claim 6, further comprising diagnosing, treating, or diagnosing and treating a deficit or an impairment in sensorimotor function of the limb of the subject.

13. A method for diagnosing, treating, or diagnosing and treating a deficit or an impairment in sensorimotor function of a limb of a subject, comprising:

coupling a virtual joint of a first robotic mechanical linkage to a first selected joint limb of the subject;

wherein an axis of the virtual joint is not located on the first robotic mechanical linkage;

wherein the first robotic mechanical linkage is not located on or along an axis of the coupled first selected joint of the limb;

wherein the first robotic mechanical linkage includes a second joint that is not located on an axis of the first selected joint of the limb when the limb is coupled to the linkage; and wherein the first robotic mechanical linkage includes at least two links that couple the virtual joint to the second joint of the robotic mechanical linkage;

wherein coupling provides that motion or torque about an axis at one or more selected joint of the limb will produce a related motion or torque about an axis of one or more selected joint or link of the robotic mechanical linkage;

the method further comprising:

engaging the limb of the subject in a task involving articulation of at least the first selected joint of the limb;

using one or more sensor with the robotic mechanical linkage, wherein the one or more sensor provides one or more signal corresponding to at least one of angular position, torque, and acceleration of at least one joint or link of the robotic mechanical linkage;

processing the one or more signal to generate data, the data corresponding to at least one of angular position, torque, and acceleration of one or more joints of the limb during the task; and using the data to diagnose, treat, or diagnose and treat the deficit or impairment in sensorimotor function of the limb of the subject.

14. The method of claim 13, further comprising:

coupling a second robotic mechanical linkage to a second selected joint of the limb, the second robotic mechanical linkage including links for coupling the second robotic mechanical linkage to the second selected joint, with at least one joint having articulation about an axis;

wherein a joint of the second robotic mechanical linkage is located on or along an axis of the second selected joint of the limb.

15. The method of claim 14, further comprising:
coupling a third robotic mechanical linkage to a third selected joint of the limb, the third robotic mechanical linkage including links for coupling the third robotic mechanical linkage to the third selected joint, with at least one joint having articulation about an axis;
wherein a joint of the third robotic mechanical linkage is located on or along an axis of the third selected joint of the limb.

16. The method of claim 13, further comprising:
coupling a second robotic mechanical linkage to the first selected joint of the limb, the first and second robotic mechanical linkages providing two degrees of freedom to the first selected joint; or
coupling a second robotic mechanical linkage and a third robotic mechanical linkage to the first selected joint of the limb, the first, second, and third robotic mechanical linkages providing three degrees of freedom to the first selected joint;
wherein the second robotic mechanical linkage includes links for coupling the second robotic mechanical linkage to the first selected joint and having articulation about an axis that corresponds to a second axis of rotation of the first selected joint of the limb; and
wherein the third robotic mechanical linkage includes links for coupling the third robotic mechanical linkage to the first selected joint and having articulation about an axis that corresponds to a third axis of rotation of the first selected joint of the limb.

17. The method of claim 16, further comprising one of:
(i) coupling a third robotic mechanical linkage to a second selected joint of the limb of the subject;
(ii) coupling a third robotic mechanical linkage to a second selected joint of the limb of the subject and coupling a fourth robotic mechanical linkage to the second selected joint of the limb of the subject, the third and fourth robotic mechanical linkages providing two degrees of freedom to the second selected joint; and
(iii) coupling a third robotic mechanical linkage to a second selected joint of the limb of the subject, coupling a fourth robotic mechanical linkage to the second selected joint of the limb of the subject, and coupling a fifth robotic mechanical linkage to the second selected joint of the limb of the subject, the third, fourth, and fifth robotic mechanical linkages providing three degrees of freedom to the second selected joint;
wherein the second robotic mechanical linkage includes links for coupling the second robotic mechanical linkage to the first selected joint and having articulation about an axis that corresponds to a second axis of rotation of the first selected joint of the limb;
wherein the third robotic mechanical linkage includes links for coupling the third robotic mechanical linkage to the second selected joint and having articulation about an axis that corresponds to a first axis of rotation of the second selected joint of the limb;
wherein the fourth robotic mechanical linkage includes links for coupling the fourth robotic mechanical linkage to the second selected joint and having articulation about an axis that corresponds to a second axis of rotation of the second selected joint of the limb; and
wherein the fifth robotic mechanical linkage includes links for coupling the fifth robotic mechanical linkage to the second selected joint and having articulation about an axis that corresponds to a third axis of rotation of the second selected joint of the limb.

18. A method for diagnosing, treating, or diagnosing and treating a deficit or an impairment in sensorimotor function of a limb of a subject, comprising:
coupling a first robotic mechanical linkage to a first selected joint of a limb of a subject, the first robotic mechanical linkage including at least two links for coupling the first robotic mechanical linkage to the first selected joint and having articulation about a first axis that corresponds to an axis of rotation of the first selected joint of the limb;
engaging the limb of the subject in a task involving articulation of at least the first selected joint of the limb;
using one or more sensor with the robotic mechanical linkage, wherein the one or more sensor provides one or more signal corresponding to at least one of angular position, torque, and acceleration of at least one joint or link of the robotic mechanical linkage;
processing the one or more signal to generate data, the data corresponding to at least one of angular position, torque, and acceleration of one or more joints of the limb during the task; and
using the data to diagnose, treat, or diagnose and treat the deficit or impairment in sensorimotor function;
wherein the first axis of rotation of the first robotic mechanical linkage is substantially collinear with the axis of rotation of the first selected joint of the limb;
wherein a second axis of rotation of the first robotic mechanical linkage is substantially collinear with an axis of rotation of a second selected joint of the limb, the second selected joint of the limb being the next joint which is distal or proximal to the first selected joint of the limb; and
wherein a distance between the first and second axes of rotation of the first robotic mechanical linkage is variable and coupling of the first and second axes of rotation is maintained without adjusting length of links of the first robotic mechanical linkage.

* * * * *